(12) United States Patent
Schmitt et al.

(10) Patent No.: US 7,655,784 B2
(45) Date of Patent: Feb. 2, 2010

(54) **TRANS-SIALIDASES OBTAINED FROM *TRYPANOSOMA CONGOLENSE***

(75) Inventors: Joachim Schmitt, Hosbach (DE); Gunter Boehm, Echzell (DE); Bernd Stahl, Rosbach (DE); Roland Schauer, Altenholz (DE); Evelin Tiralongo, Neubrandenburg (DE); Silke Schrader, Kiel (DE)

(73) Assignee: N.V. Nutricia, HM Zoetermeer H.M. (NL)

( * ) Notice: Subject to any disclaimer, the term of this patent is extended or adjusted under 35 U.S.C. 154(b) by 7 days.

(21) Appl. No.: 10/538,840

(22) PCT Filed: Dec. 11, 2003

(86) PCT No.: PCT/EP03/14079
§ 371 (c)(1),
(2), (4) Date: Mar. 1, 2006

(87) PCT Pub. No.: WO2004/055176
PCT Pub. Date: Jul. 1, 2004

(65) Prior Publication Data
US 2007/0004656 A1   Jan. 4, 2007

(30) Foreign Application Priority Data
Dec. 13, 2002 (DE) .................. 102 58 400

(51) Int. Cl.
C07H 21/02 (2006.01)
C07H 21/04 (2006.01)
A61K 39/00 (2006.01)

(52) U.S. Cl. ............ 536/23.7; 536/23.1; 530/300; 530/350; 424/184.1; 424/185.1; 424/190.1; 424/191.1

(58) Field of Classification Search ............ 424/184.1, 424/185.1, 190.1, 191.1, 9.1, 9.2, 234.1, 424/248.1; 530/300, 350; 536/23.1, 23.7
See application file for complete search history.

(56) References Cited
OTHER PUBLICATIONS

Pontes De Carvalho Lain C. et al., "Characterization of a novel trans-sialidase of *Trypanosoma brucei* procyclic trypomastigotes and identification of procyclin as the main sialic acid acceptor", Journal of Experimental Medicine, vol. 177, No. 2, 1993, pp. 465-474, XP002276140.

Montagna Georgina et al., "The trans-sialidase from the African trypanosome *Trypanosoma brucei*", European Jounal of Biochemistry, vol. 269, No. 12, Jun. 2002, pp. 2941-2950, XP002276141 & Database EMBL retrieved from EBI Database accession No. AF310232, abstract.

Database EMBL XP002276142 retrieved from EBI Database accession No. AF181287, abstract.

Cremona M. L. et al., "A single tryosine differentiates active and inactive *Trypanosoma cruzi* trans-sialidases", Gene, Elsevier Biomedical Press, Amsterdam, NL, vol. 160, No. 1, Jul. 4, 1995, pp. 123-128, XP004042190 & Database EMBL retrieved from EBI Database accession No. Q26968 Trans-sialidase 45, abstract.

Tiralongo Evelin et al., "Two trans-sialidase forms with different sialic acid transfer and sialidase activites from *Trypanosoma congolense*," Journal of Biological Chemistry, vol. 278, No. 26, Jun. 27, 2003, pp. 23301-23310, XP002293242 & Databse EMBL retrieved from EBI Database accession No. Q7YZT2, Trans-Sialidase, abstract.

Engstler Markus et al., "The developmentally regulated trans-sialidase from *Trypanosoma brucei* sialylates the procyclic acidic repetitive protein", Molecular and Biochemical Parasitology, vol. 61, No. 1, 1993, pp. 1-13, XP002293243.

*Primary Examiner*—Rodney P. Swartz
(74) *Attorney, Agent, or Firm*—Bacon & Thomas, PLLC

(57) ABSTRACT

The invention relates to novel enzymes, which transfer sialic acid from a donor molecule onto an acceptor molecule (trans-sialidases). The enzymes are isolated from the protozoan *Trypanosoma congolense*. The invention also relates to functional equivalents of said enzymes, to the nucleic acid sequences and amino acid sequences that code for the enzymes and their functional equivalents, to expression constructs and vectors that contain said sequences, to recombinant microorganisms that carry the inventive coding nucleic-acid sequences, to a method for the recombinant production of the inventive enzymes, to a method for isolating said enzyme from *Trypanosoma congolense*, to a method for the enzymatic sialization of acceptor molecules using the inventive enzymes, to effectors of the inventive trans-sialidases, to the use of the nucleic acid sequences, amino acid sequences, enzymes, effectors or sialization products for producing vaccines, medicaments, foodstuffs or food additives, in addition to the latter products obtained by the inventive method.

18 Claims, 3 Drawing Sheets

Figure 2

Sialidase
Hydrolysis of donor boded silalic acids

Y-Neu5Ac + H$_2$O  ⟶  Neu5Ac + Y

Sialyltransferase
Transfer of sialic acids activated with CMP to acceptor molecules CMP-Neu5Ac + X  ⟶  X-Neu5Ac + CMP

Trans-sialidase
Transfer of sialic acids from donor to acceptor molecules

Y-Neu5Ac + X-Gal  ⟶  X-Gal-Neu5Ac + Y

SEQUENCE LISTING

```
<160> NUMBER OF SEQ ID NOS: 4

<210> SEQ ID NO 1
<211> LENGTH: 1491
<212> TYPE: DNA
<213> ORGANISM: Trypanosoma congolense
<220> FEATURE:
<221> NAME/KEY: CDS
<222> LOCATION: (1)..(1491)
<223> OTHER INFORMATION:

<400> SEQUENCE: 1 acc gac acc gtt gct aaa tac agc act gac ggt ggg aga acg tgg aag      48
Thr Asp Thr Val Ala Lys Tyr Ser Thr Asp Gly Gly Arg Thr Trp Lys
1               5                   10                  15 agg gag gtt ata att ccg aat ggt cgt gtg gat gcc cac tac tcc cgc      96
Arg Glu Val Ile Ile Pro Asn Gly Arg Val Asp Ala His Tyr Ser Arg
                20                  25                  30 gtc gtt gat ccc act gtt gtt gcg aag ggt aat aac att tat gtt ctc     144
Val Val Asp Pro Thr Val Val Ala Lys Gly Asn Asn Ile Tyr Val Leu
            35                  40                  45 gtt ggg cgg tac aat gtc acg cgg ggc tac tgg cac aat agg aac aac     192
Val Gly Arg Tyr Asn Val Thr Arg Gly Tyr Trp His Asn Arg Asn Asn
        50                  55                  60 aag gct ggc ata gcc gat tgg gag ccc ttc gtg tac aag ggc acg gtg     240
Lys Ala Gly Ile Ala Asp Trp Glu Pro Phe Val Tyr Lys Gly Thr Val
65                  70                  75                  80
```

```
                                                                    -continued aac gtg ggc acg aag ggc aat gcc act gat gtg tcg atc agc tgg gag      288
Asn Val Gly Thr Lys Gly Asn Ala Thr Asp Val Ser Ile Ser Trp Glu
                 85                  90                  95 agg act gca ctg aag tcg ctg tac aac ttc ccg gtt tcg gga agc cct      336
Arg Thr Ala Leu Lys Ser Leu Tyr Asn Phe Pro Val Ser Gly Ser Pro
            100                 105                 110 ggc acg cag ttc ctt gga ggg gct ggg ggt ggt gtt gta aca tcc aac      384
Gly Thr Gln Phe Leu Gly Gly Ala Gly Gly Gly Val Val Thr Ser Asn
        115                 120                 125 ggg acg att gtg ctg cca gtg cag gca agg aac aag gcc aac cgt gtt      432
Gly Thr Ile Val Leu Pro Val Gln Ala Arg Asn Lys Ala Asn Arg Val
    130                 135                 140 gtg agc atg atc ctg tac tcg gct gac gat gga aag tca tgg cac ttt      480
Val Ser Met Ile Leu Tyr Ser Ala Asp Asp Gly Lys Ser Trp His Phe
145                 150                 155                 160 ggg aag ggt gag gcc ggt gta ggc acg tcc gag gct gcc ctc act gag      528
Gly Lys Gly Glu Ala Gly Val Gly Thr Ser Glu Ala Ala Leu Thr Glu
                165                 170                 175 tgg gac ggc aag ctg ctg att agt gca cga tcc gat ggt gga cag ggc      576
Trp Asp Gly Lys Leu Leu Ile Ser Ala Arg Ser Asp Gly Gly Gln Gly
            180                 185                 190 tac cgc atg ata ttc gaa tcg agt gac ctt ggt gcg acg tgg aaa gag      624
Tyr Arg Met Ile Phe Glu Ser Ser Asp Leu Gly Ala Thr Trp Lys Glu
        195                 200                 205 atg ctc aac agc atc tcc cgc gtg att ggc aac tct ccg ggt cgc agt      672
Met Leu Asn Ser Ile Ser Arg Val Ile Gly Asn Ser Pro Gly Arg Ser
    210                 215                 220 ggt cct ggc agc tcg agt ggc ttc atc acg gtg aca gtg gag ggt gtg      720
Gly Pro Gly Ser Ser Ser Gly Phe Ile Thr Val Thr Val Glu Gly Val
225                 230                 235                 240 cct gtg atg ctg att acc cac ccg aag aac ctt aag ggc tcg tat tat      768
Pro Val Met Leu Ile Thr His Pro Lys Asn Leu Lys Gly Ser Tyr Tyr
                245                 250                 255 cgg gac cgt ctg cag ctg tgg atg acg gac ggc aat cgt atg tgg cat      816
Arg Asp Arg Leu Gln Leu Trp Met Thr Asp Gly Asn Arg Met Trp His
            260                 265                 270 gtc ggg cag gtc tct gag ggc gac gat aac agc gct tac agc tcc ctg      864
Val Gly Gln Val Ser Glu Gly Asp Asp Asn Ser Ala Tyr Ser Ser Leu
        275                 280                 285 ctg tac act ccg gac ggg gtc ctg tac tgc ttg cat gag cag aac att      912
Leu Tyr Thr Pro Asp Gly Val Leu Tyr Cys Leu His Glu Gln Asn Ile
    290                 295                 300 gat gag gtg tac agc ctc cac ctt gtg cgc ctt gtg gac gag ctg aaa      960
Asp Glu Val Tyr Ser Leu His Leu Val Arg Leu Val Asp Glu Leu Lys
305                 310                 315                 320 agc att aaa tca acg gct ctg gtg tgg aag gca cag gac gag ctt ctc     1008
Ser Ile Lys Ser Thr Ala Leu Val Trp Lys Ala Gln Asp Glu Leu Leu
                325                 330                 335 ctg ggc aac tgc ctc ccg ggc gat aaa tac gat ccc ggg tgt gac ggc     1056
Leu Gly Asn Cys Leu Pro Gly Asp Lys Tyr Asp Pro Gly Cys Asp Gly
            340                 345                 350 atc ccc acc gct ggg ctt gcc ggg ctg ctg gta gga ccc ctg acg gag     1104
Ile Pro Thr Ala Gly Leu Ala Gly Leu Leu Val Gly Pro Leu Thr Glu
        355                 360                 365 aag acg tgg ccc gac gcg tat cgg tgc gtg aac gct gca acc agc ggc     1152
Lys Thr Trp Pro Asp Ala Tyr Arg Cys Val Asn Ala Ala Thr Ser Gly
    370                 375                 380 gct gtg agc act gct gaa ggc gtg cgg ctg gac gtg ggt ggc ggt ggc     1200
Ala Val Ser Thr Ala Glu Gly Val Arg Leu Asp Val Gly Gly Gly Gly
385                 390                 395                 400
```

```
cat gtt gtg tgg ccc gtg agt gag cag ggg cag gac cag cgg tat tac      1248
His Val Val Trp Pro Val Ser Glu Gln Gly Gln Asp Gln Arg Tyr Tyr
            405                 410                 415 ttt acc aac agc gag ttc acg ctc gcc gtc acg gtg cgg ttt gac gag      1296
Phe Thr Asn Ser Glu Phe Thr Leu Ala Val Thr Val Arg Phe Asp Glu
        420                 425                 430 atg cca cgg ggg gag ctc ccg ttg ctg ggg ttt gtg aac cgc aaa ggg      1344
Met Pro Arg Gly Glu Leu Pro Leu Leu Gly Phe Val Asn Arg Lys Gly
    435                 440                 445 aag gtg aag aag ata ctg aag gtg tcg ctg agc ggg gtg gag tgg ctc      1392
Lys Val Lys Lys Ile Leu Lys Val Ser Leu Ser Gly Val Glu Trp Leu
450                 455                 460 ctg gca tac ggg aat gag tac aac agc aca gcc gct gag ccg ctg gac      1440
Leu Ala Tyr Gly Asn Glu Tyr Asn Ser Thr Ala Ala Glu Pro Leu Asp
465                 470                 475                 480 gtg aac gag agc cac cag gtg gtg cta gcg ctt cac gac ggg atc gtc      1488
Val Asn Glu Ser His Gln Val Val Leu Ala Leu His Asp Gly Ile Val
                485                 490                 495 tcc                                                                  1491
Ser

<210> SEQ ID NO 2
<211> LENGTH: 497
<212> TYPE: PRT
<213> ORGANISM: Trypanosoma congolense

<400> SEQUENCE: 2

Thr Asp Thr Val Ala Lys Tyr Ser Thr Asp Gly Gly Arg Thr Trp Lys
1               5                   10                  15

Arg Glu Val Ile Ile Pro Asn Gly Arg Val Asp Ala His Tyr Ser Arg
            20                  25                  30

Val Val Asp Pro Thr Val Ala Lys Gly Asn Asn Ile Tyr Val Leu
        35                  40                  45

Val Gly Arg Tyr Asn Val Thr Arg Gly Tyr Trp His Asn Arg Asn Asn
    50                  55                  60

Lys Ala Gly Ile Ala Asp Trp Glu Pro Phe Val Tyr Lys Gly Thr Val
65                  70                  75                  80

Asn Val Gly Thr Lys Gly Asn Ala Thr Asp Val Ser Ile Ser Trp Glu
                85                  90                  95

Arg Thr Ala Leu Lys Ser Leu Tyr Asn Phe Pro Val Ser Gly Ser Pro
            100                 105                 110

Gly Thr Gln Phe Leu Gly Ala Gly Gly Val Val Thr Ser Asn
        115                 120                 125

Gly Thr Ile Val Leu Pro Val Gln Ala Arg Asn Lys Ala Asn Arg Val
    130                 135                 140

Val Ser Met Ile Leu Tyr Ser Ala Asp Asp Gly Lys Ser Trp His Phe
145                 150                 155                 160

Gly Lys Gly Glu Ala Gly Val Gly Thr Ser Glu Ala Ala Leu Thr Glu
                165                 170                 175

Trp Asp Gly Lys Leu Leu Ile Ser Ala Arg Ser Asp Gly Gln Gly
            180                 185                 190

Tyr Arg Met Ile Phe Glu Ser Ser Asp Leu Gly Ala Thr Trp Lys Glu
        195                 200                 205

Met Leu Asn Ser Ile Ser Arg Val Ile Gly Asn Ser Pro Gly Arg Ser
    210                 215                 220

Gly Pro Gly Ser Ser Ser Gly Phe Ile Thr Val Thr Val Glu Gly Val
225                 230                 235                 240
```

-continued

```
Pro Val Met Leu Ile Thr His Pro Lys Asn Leu Lys Gly Ser Tyr Tyr
                245                 250                 255

Arg Asp Arg Leu Gln Leu Trp Met Thr Asp Gly Asn Arg Met Trp His
            260                 265                 270

Val Gly Gln Val Ser Glu Gly Asp Asp Asn Ser Ala Tyr Ser Ser Leu
        275                 280                 285

Leu Tyr Thr Pro Asp Gly Val Leu Tyr Cys Leu His Glu Gln Asn Ile
    290                 295                 300

Asp Glu Val Tyr Ser Leu His Leu Val Arg Leu Val Asp Glu Leu Lys
305                 310                 315                 320

Ser Ile Lys Ser Thr Ala Leu Val Trp Lys Ala Gln Asp Glu Leu Leu
                325                 330                 335

Leu Gly Asn Cys Leu Pro Gly Asp Lys Tyr Asp Pro Gly Cys Asp Gly
            340                 345                 350

Ile Pro Thr Ala Gly Leu Ala Gly Leu Leu Val Gly Pro Leu Thr Glu
        355                 360                 365

Lys Thr Trp Pro Asp Ala Tyr Arg Cys Val Asn Ala Ala Thr Ser Gly
    370                 375                 380

Ala Val Ser Thr Ala Glu Gly Val Arg Leu Asp Val Gly Gly Gly
385                 390                 395                 400

His Val Val Trp Pro Val Ser Glu Gln Gly Gln Asp Gln Arg Tyr Tyr
                405                 410                 415

Phe Thr Asn Ser Glu Phe Thr Leu Ala Val Thr Val Arg Phe Asp Glu
            420                 425                 430

Met Pro Arg Gly Glu Leu Pro Leu Leu Gly Phe Val Asn Arg Lys Gly
        435                 440                 445

Lys Val Lys Lys Ile Leu Lys Val Ser Leu Ser Gly Val Glu Trp Leu
    450                 455                 460

Leu Ala Tyr Gly Asn Glu Tyr Asn Ser Thr Ala Ala Glu Pro Leu Asp
465                 470                 475                 480

Val Asn Glu Ser His Gln Val Val Leu Ala Leu His Asp Gly Ile Val
                485                 490                 495

Ser
```

<210> SEQ ID NO 3
<211> LENGTH: 831
<212> TYPE: DNA
<213> ORGANISM: Trypanosoma congolense
<220> FEATURE:
<221> NAME/KEY: CDS
<222> LOCATION: (1)..(831)
<223> OTHER INFORMATION:

<400> SEQUENCE: 3

```
ttc cga att ccc tca ctt gtt gag ata gac ggc gtg ctt atc gcg aca    48
Phe Arg Ile Pro Ser Leu Val Glu Ile Asp Gly Val Leu Ile Ala Thr
1               5                   10                  15 ttc gat aca cgt tat ctt cgc gct tcc gac agc agt ctc ata gac aca    96
Phe Asp Thr Arg Tyr Leu Arg Ala Ser Asp Ser Ser Leu Ile Asp Thr
            20                  25                  30 gct atg aaa tac agt gcc gat cag ggg aag acg tgg aaa act gaa atc   144
Ala Met Lys Tyr Ser Ala Asp Gln Gly Lys Thr Trp Lys Thr Glu Ile
        35                  40                  45 ata ata aaa aat gct aga cta act gat aac ttt tcc cgc gtc gtt gat   192
Ile Ile Lys Asn Ala Arg Leu Thr Asp Asn Phe Ser Arg Val Val Asp
    50                  55                  60
```

-continued

```
cca acg gtt gtt gtt aag ggt gat aac ttg ttt att ttt gtt ggg agg     240
Pro Thr Val Val Val Lys Gly Asp Asn Leu Phe Ile Phe Val Gly Arg
 65                  70                  75                  80 tac aac acc tca tct gcc cca tgg gtc tgg cag gaa aac ggt aaa gac     288
Tyr Asn Thr Ser Ser Ala Pro Trp Val Trp Gln Glu Asn Gly Lys Asp
                 85                  90                  95 tgg gat gta ctg ttg tac aag gcc aag gtg agg aag gaa tca gcg ggt     336
Trp Asp Val Leu Leu Tyr Lys Ala Lys Val Arg Lys Glu Ser Ala Gly
            100                 105                 110 ggg gta cca tca gtg agc ttt aca tgg gac gaa ccc cta tac ctg aag     384
Gly Val Pro Ser Val Ser Phe Thr Trp Asp Glu Pro Leu Tyr Leu Lys
        115                 120                 125 cat ctg ctc acc tct gtc ggt aaa ata gac ggc agg tcc ctc ata caa     432
His Leu Leu Thr Ser Val Gly Lys Ile Asp Gly Arg Ser Leu Ile Gln
    130                 135                 140 tac att ggt ggc gtt gga aat ggt att gta aca ccg aaa ggt act atc     480
Tyr Ile Gly Gly Val Gly Asn Gly Ile Val Thr Pro Lys Gly Thr Ile
145                 150                 155                 160 gtg ttt cca gtt cag gtt tta aac acc aac aaa tcc gtc atg aac atg     528
Val Phe Pro Val Gln Val Leu Asn Thr Asn Lys Ser Val Met Asn Met
                165                 170                 175 ctt ctg tat tca agt aac gac gga aaa acc tgg gag ttc agc aaa act     576
Leu Leu Tyr Ser Ser Asn Asp Gly Lys Thr Trp Glu Phe Ser Lys Thr
            180                 185                 190 tcc aca ccc gcg ggc aca act gag gcc tcc ctt gtt tgg tgg gat gga     624
Ser Thr Pro Ala Gly Thr Thr Glu Ala Ser Leu Val Trp Trp Asp Gly
        195                 200                 205 caa cta ctt ctc aca agc aga aca act ccg gat gtc ggc agc cgc aaa     672
Gln Leu Leu Leu Thr Ser Arg Thr Thr Pro Asp Val Gly Ser Arg Lys
    210                 215                 220 gta tat tta aca agc gac ctc gga act tca tgg aat gaa gcg atc gga     720
Val Tyr Leu Thr Ser Asp Leu Gly Thr Ser Trp Asn Glu Ala Ile Gly
225                 230                 235                 240 agt atc tct cgt gta att ggt aac tcg cgg tac cgt aac gat cct ggg     768
Ser Ile Ser Arg Val Ile Gly Asn Ser Arg Tyr Arg Asn Asp Pro Gly
                245                 250                 255 ggg tca ggt agc tca att gcc ata act gtg gag gga gta ccg gtg atg     816
Gly Ser Gly Ser Ser Ile Ala Ile Thr Val Glu Gly Val Pro Val Met
            260                 265                 270 ctg att acc cac ccg                                                 831
Leu Ile Thr His Pro
        275
```

<210> SEQ ID NO 4
<211> LENGTH: 277
<212> TYPE: PRT
<213> ORGANISM: Trypanosoma congolense

<400> SEQUENCE: 4

```
Phe Arg Ile Pro Ser Leu Val Glu Ile Asp Gly Val Leu Ile Ala Thr
  1               5                  10                  15

Phe Asp Thr Arg Tyr Leu Arg Ala Ser Asp Ser Ser Leu Ile Asp Thr
                 20                  25                  30

Ala Met Lys Tyr Ser Ala Asp Gln Gly Lys Thr Trp Lys Thr Glu Ile
            35                  40                  45

Ile Ile Lys Asn Ala Arg Leu Thr Asp Asn Phe Ser Arg Val Val Asp
        50                  55                  60

Pro Thr Val Val Val Lys Gly Asp Asn Leu Phe Ile Phe Val Gly Arg
 65                  70                  75                  80
```

-continued

| | | | | | | | | | | | | |
|---|---|---|---|---|---|---|---|---|---|---|---|---|
|Tyr|Asn|Thr|Ser 85|Ser|Ala|Pro|Trp|Val 90|Trp|Gln|Glu|Asn|Gly|Lys 95|Asp|
|Trp|Asp|Val|Leu 100|Leu|Tyr|Lys|Ala|Lys 105|Val|Arg|Lys|Glu|Ser 110|Ala|Gly|
|Gly|Val|Pro 115|Ser|Val|Ser|Phe|Thr 120|Trp|Asp|Glu|Pro|Leu 125|Tyr|Leu|Lys|
|His|Leu|Leu 130|Thr|Ser|Val|Gly|Lys 135|Ile|Asp|Gly|Arg 140|Ser|Leu|Ile|Gln|
|Tyr 145|Ile|Gly|Gly|Val|Gly 150|Asn|Gly|Ile|Val|Thr 155|Pro|Lys|Gly|Thr|Ile 160|
|Val|Phe|Pro|Val|Gln 165|Val|Leu|Asn|Thr|Asn 170|Lys|Ser|Val|Met|Asn 175|Met|
|Leu|Leu|Tyr|Ser 180|Ser|Asn|Asp|Gly|Lys 185|Thr|Trp|Glu|Phe|Ser 190|Lys|Thr|
|Ser|Thr|Pro 195|Ala|Gly|Thr|Thr|Glu 200|Ala|Ser|Leu|Val|Trp 205|Trp|Asp|Gly|
|Gln|Leu 210|Leu|Leu|Thr|Ser|Arg 215|Thr|Thr|Pro|Asp|Val 220|Gly|Ser|Arg|Lys|
|Val|Tyr 225|Leu|Thr|Ser|Asp 230|Leu|Gly|Thr|Ser|Trp 235|Asn|Glu|Ala|Ile|Gly 240|
|Ser|Ile|Ser|Arg|Val 245|Ile|Gly|Asn|Ser|Arg 250|Tyr|Arg|Asn|Asp|Pro 255|Gly|
|Gly|Ser|Gly|Ser 260|Ser|Ile|Ala|Ile|Thr 265|Val|Glu|Gly|Val|Pro 270|Val|Met|
|Leu|Ile|Thr|His 275|Pro| | | | | | | | | | | |

TRANS-SIALIDASES OBTAINED FROM *TRYPANOSOMA CONGOLENSE*

SUBJECT MATTER OF THE INVENTION

The invention relates to novel enzymes which transfer the sialic acids from a donor molecule (eg. oligosaccharides, polysialic acids, glycosylated proteins, glycosylated peptides, glycosylated lipids (eg. ganglioside) and other glycosylated low or high molecular molecules) onto an acceptor molecule (eg. oligo- and polysaccharides, glycosylated proteins, glycosylated peptides, glycosylated lipids and other glycosylated low and high molecular molecules) (trans-sialidases). The enzymes were isolated from the protozoan *Trypanosoma congolense*.

The invention also relates to functional equivalents of said enzymes; to the nucleic acid sequences that code for these enzymes and their functional equivalents; to expression constructs and vectors that contain said sequences; to recombinant micro-organisms that carry a coding nucleic acid sequence in accordance with the invention; to a method for the recombinant production of enzymes in accordance with the invention; to a method for isolating the enzymes in accordance with the invention from *Trypanosoma congolense*; to a method for the enzymatic sialization of acceptor molecules using the enzymes in accordance with the invention; to effectors of the trans-sialidases in accordance with the invention; to the use of the nucleic acid sequences, enzymes, effectors or sialization products in accordance with the invention for producing vaccines, medicaments, foodstuffs or food additives; and to the agents themselves produced in accordance with the invention.

BACKGROUND TO THE INVENTION

Trans-sialidases can transfer sialic acids, preferably alpha-2,3-bonded sialic acids, from a donor molecule to an acceptor molecule, whereby again, alpha-2,3-glycosidic bonds can be formed, preferably on a β-terminal galactose residue.

The term sialic acids includes all N and O derivatives of neuraminic acid (Blix et al, 1957). Neuraminic acid (5-amino-3,5-didesoxy-D-glycero-D-galacto-nonulo-pyranosonic acid) is an amino sugar with a backbone consisting of nine carbon atoms, which acquires a very acid pK value of 2,2 due to the carboxyl group on the C atom 2, and so is negatively charged under physiological conditions.

The non-substituted form is very unstable and does not occur in nature in free form (Schauer, 1982). However, more than 40 natural derivatives of neuraminic acid are meanwhile known (Schauer and Kamerling, 1997). The two sialic acids which most frequently occur in nature are the N-acetylneuraminic acid (Neu5Ac), the forerunner of all glycosidically bonded sialic acids (Schauer, 1991) and the N-glycolylneuraminic acid (Neu5Gc) which emerges by means of hydroxylation of the methyl group of the N-acetyl residue of CMP-Neu5Ac (Shaw and Schauer, 1988). The hydroxyl groups of these two sialic acids can be substituted by acetyl, lactyl, methyl, sulphate and phosphate residues in different combinations, and this leads to the great structural variety of the sialic acids (Schauer, 1991; Schauer and Kamerling, 1997).

The greatest number of the naturally occurring sialic acids are bonded as a component part of oligosaccharides, polysaccharides and in particular glycoconjugates (Schauer, 1982). However, polysialic acids are also known from transgenic microbe production. Sialated glycoconjugates mainly occur in the outer membrane of cells, but are however important components of the serum of mucosa (Traving and Schauer, 1998). The sialic acids protect glycoproteins and cells from attack by proteases and other enzymes, and so from decomposition (Reuter et al., 1988). The mucosa of the gastrointestinal tract which contain sialic acid not only form effective protection from the digestion enzymes, but also protect the tissues lying among these from the penetration of pathogenic bacteria (Kalm and Schauer, 1997).

Sialic acids fulfil a very important function with molecular and cellular identification processes. Here, they conceal receptors and so prevent interactions between receptors and ligands (Schauer, 1985; Kelm and Schauer, 1997). Sialic acids therefore protect eg. serum glycoproteins and erythrocytes against decomposition and phagocytosis whereby they conceal galactose residues present here. If the terminal sialic acids are separated, the subterminal galactose residues can be bonded by lectins on hepatocytes or phagocytes, and the result is endocytosis of the serum proteins or erythrocytes. A further example is the protection of the body's own tissues, but also of many highly sialated tumours before identification by the immune system (Pilatte et al., 1993). If the protective sialic acid layer is lost, autoimmune reactions can occur.

Sialic acids also serve as identification points for the body's own cells and hormones, and so play an important role in cellular interactions (Kelm and Schauer, 1997). With inflammation, endothel cells express selectins on their surface which identify certain sialated structures (eg. sialyl Lewis X) on leucocytes so that the same bind to the endothel cells and can penetrate into the tissue (Lasky, 1995). Furthermore, the activation of the T-cells of the humoral immune defence is influenced by the effect of trans-sialidases (Gao et al., 2001). Sialoadhesins (siglecs) such as the myelin-associated glycoprotein (MAG) also bind highly specifically onto sialated glycans (Kelm et al., 1996; Crocker et al., 1998). In the nervous system, the myelin-associated glycoprotein is involved, among other things, in the myelinisation and in the regulation of axonal growth. It is therefore not astonishing that it was recently discovered that trans-sialidases are involved by the transfer of sialic acids in the differentiation of nerve cells and glia cells (Chuenkova et al., 2001). CD-22 is another sialic acid-binding receptor which occurs on lymphocytes and makes possible the "dialogue" of T- and B-lymphocytes. The siglecs family consists on average of more than 10 molecular-biologically characterised representatives.

Sialic acids are however not only important with the body's own identification processes, but are also receptors for certain bacteria, viruses and toxins. For example, the binding of the tetanus toxin to gangliosides of nerve synapses happens by means of sialic acids (Schauer et al., 1995). The sialic acid-specific adhesion by means of microbial lectins (Sharon and Lis, 1997) is often a critical step with infectious diseases, for example with newborn meningitis brought about by some *E. coil* stems or with infections of the gastric mucosa by means of *Helicobacter pylori*. Above all, the flu viruses Influenza A and B viruses attach onto the cells to be infected by means of sialic acid (Schauer, 2000).

Modifications of the sialic acids, in particular the O-acetylation, are of great significance in the regulation of molecular and cellular identification (Schauer, 1991). Influenza C viruses thus bind specifically to 9-O-acetylated sialic acids on bronchial epithels (Herrier et al., 1985), whereas the O-acetylation prevents binding of the influenza A and B viruses (Higa et al., 1985). Above all, however, the O-acetylation of sialic acids is very important for the morphogenesis and development of different tissues (Varki et al., 1991). With neuroectodermal tumours it is increased (Hubi et al., 2000; Fahr and Schauer, 2001), and with cancer of the colon it is decreased (Corfield et al., 1999). Sialic acids are essential modulators of the biological behaviour of tumours (Schauer, 2000).

DESCRIPTION OF THE FIGURES

FIG. 2 shows the different reactions of sialidase, sialyltransferases and trans-sialidases.

SHORT DESCRIPTION OF THE INVENTION

Figure 1:
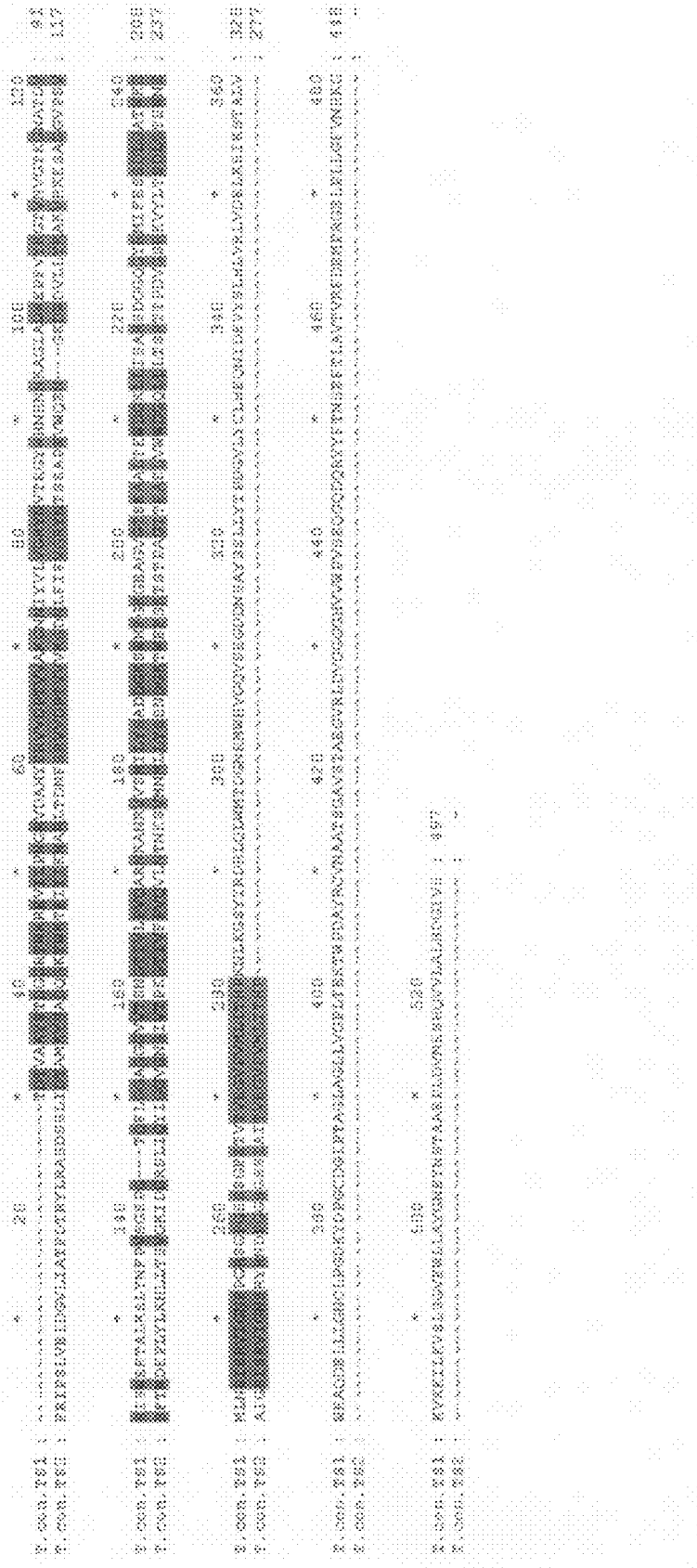
FIG. 1 shows a comparison of the amino acid part sequences of the trans-sialidases TS1 (SEQ ID NO. 2) and TS2 (SEQ ID NO. 4) in accordance with the invention. Identical amino acids in both sequences are indicated in bold. The correspondence (sameness) of the two part sequences is only approximately 50%.

The aim of this invention was to provide a novel means with which it would be possible to influence biological or patho-biological processes controlled by sialic acid.

Surprisingly, it was possible to fulfil the above task by providing novel enzymes with trans-sialidase activity and the coding sequences of the same from *Trypanosoma congolense*.

A first subject matter area of the invention relates to polynucleotides which code for proteins with trans-sialidase activity and can be isolated from *Trypanosoma congolense*, whereby these proteins preferably catalyse the transfer of sialic acid from a donor to an acceptor molecule.

Preferred polynucleotides comprise at least one nucleic acid sequence in accordance with SEQ ID NO: 1 or 3, or are fragments of the same which comprise at least 15 connected nucleotide residues. The subject matter of the invention also includes the polynucleotides and fragments complementary to these; and the nucleotide sequences derived from these polynucleotides by degeneration of the genetic code.

The subject matter of the invention also includes oligonucleotides which hybridise with a polynucleotide in accordance with the invention, in particular under stringent conditions.

The subject matter of the invention also includes polynucleotides which hybridise with an oligonucleotide in accordance with the above definition, in particular under stringent conditions, and which code for a gene product from microorganisms of the *Trypanosoma* genus.

The subject matter of the invention also includes polypeptides which can be coded from a polynucleotide which comprises a nucleic acid sequence in accordance with the above definition; or which have an amino acid sequence which comprises at least 10 connected amino acids in accordance with SEQ ID NO: 2 or 4; and functional equivalents thereof which have trans-sialidase activity.

The subject matter of the invention in particular includes trans-sialidases or functional equivalents of the same with trans-sialidase activity, characterised by one of the following amino acid part sequences: TDTVAKYSTDGGRTWKRE-VIIPNGR (pos. 1 to 25 in accordance with SEQ ID NO: 2) FRIPSLVEIDGVLIATFDTRYLRASDSSLI (pos. 1 to 30 in accordance with SEQ ID NO: 4). A preferred trans-sialidase 1 (TS1) is characterised by at least one of the following characteristics:

| Nucleotide part sequence | SEQ ID NO: 1 |
|---|---|
| Amino acid part sequence | SEQ ID NO: 2 |
| Temperature optimum | 30-40° C. |
| pH optimum | pH 6.5-8.5 |
| Isoelectric point | pH 4-5 |
| Molecular weight, native | 400-600 kDa |
| Molecular weight in the reducing SDS-page | 90 kDa |

Another preferred trans-sialidase 2 (TS2) is characterised by at least one of the following characteristics:

| Nucleotide sequence | SEQ ID NO: 3 |
|---|---|
| Amino acid part sequence | SEQ ID NO: 4 |
| Temperature optimum | 30-40° C. |
| pH optimum | pH 6.5-8.5 |
| Isoelectric point | pH 5-6 |
| Molecular weight, native | 120-180 kDa |
| Molecular weight in the reducing SDS page | 90 kDa |

The polynucleotides and polypeptides in accordance with the invention described above, in particular coding nucleic acid sequences and amino acid sequences can be derived from the organism *Trypanosoma congolense*. However, they are also accessible using synthetic, in particular chemical, biochemical, enzymatic, gene-technological and transgenic methods.

The subject matter of the invention also includes functional equivalents of the trans-sialidases in accordance with the invention.

The subject matter of the invention also includes expression cassettes, comprising a nucleic acid sequence in accordance with the above definition in operative connection with at least one regulative nucleic acid sequence. Furthermore, the invention also comprises recombinant vectors containing at least one of these expression cassettes.

The subject matter of the invention also includes procaryotic or eucaryotic hosts, transformed with at least one vector in accordance with the above definition.

Furthermore, the invention relates to the use of an expression cassette, a vector or a host in accordance with the above definition for the recombinant production of a protein with trans-sialidase activity.

The subject matter of the invention also includes a method for the enzymatic sialization of an acceptor molecule, characterised in that one incubates the acceptor molecule with a donor containing sialic acid residues in the presence of a trans-sialidase in accordance with the above definition, and isolates the sialated acceptor.

This type of method is characterised by at least one more of the following properties:

a) the donor is selected from sialic acids bonded to oligosaccharides, polysaccharides, polysialic acids, glycoproteins and glycolipids, such as in particular lactoferrins, glycolysated whey proteins and caseins and fragments of the same;

b) the acceptor is selected from polymers containing β-galactoses, such as galactooligosaccharides, lactitol, lactobionic acid, methyl-β-lactoside, acetyllactosamines, galactopyranosides, trans-galactooligosaccharides, polygalactose and other glycoconjugates with terminally bonded β(1-3) or β(14) galactose: or galactose.

A further aspect of this invention relates to the use of a trans-sialidase in accordance with the invention, of a nucleic acid sequence coding for the same or a sialization product produced in accordance with the invention for the production of a medicament, foodstuff or food additive or a food supplement for the prevention or treatment of parasitic, bacterial or viral infections controlled by sialic acid; for the treatment of tumour diseases; for the treatment of diseases which are associated with developmental interference of the tissue; for the treatment of diseases of the immune system; for the treatment of autoimmune reactions; for the treatment of diseases with interrupted cell communication; and/or for the treatment of inflammation.

In particular, the subject matter of the invention includes the use of a trans-sialidase in accordance with the invention in accordance with the above definition for the development of a Trypanosomiasis vaccine or for the development of enzyme inhibitors for the treatment or prevention of *Trypanosoma* infections.

Furthermore, the invention relates to the use of a trans-sialidase, to a nucleic acid sequence coding for the same or to a sialated product produced in accordance with the invention for the production of a medicament, food additive of foodstuff for the protection of the body's own cells or tissues or glycoproteins prior to enzymatic action.

The subject matter of the invention also includes the use of a trans-sialidase, of a nucleic acid sequence coding for the same or of a sialated product produced in accordance with the invention for the production of a medicament, food additive or food stuff so as to influence the development and/or morphogenesis of body tissues.

Furthermore, the invention relates to effectors of the trans-sialidase activity of a trans-sialidase, selected from a) polypeptide ligands which interact with a trans-sialidase in accordance with the above description;

b) low-molecular effectors which modulate the biological activity of a trans-sialidase in accordance with the above definition;

c) antisense nucleic acid sequences of a nucleic acid sequence in accordance with the above definition.

Moreover, the invention relates to the use of this type of effector for the production of a medicament, food additive or foodstuff for the treatment or prevention of diseases associated with trans-sialidase activity.

The subject matter of the invention also includes a method for isolating an enzyme with trans-sialidase activity, whereby a) *Trypanosoma congolense* is cultivated in a medium, and b) the desired product is isolated from the culture supernatant by means of ion exchange chromatography with the help of a salt gradient, if so required followed by isoelectric focussing, gel filtration, affinity chromatography and/or protein precipitation.

Finally, the invention relates to a pharmaceutical or gene-therapeutical medium containing at least one effector in accordance with the above definition in a pharmaceutically or gene-therapeutically compatible carrier.

DETAILED DESCRIPTION OF THE INVENTION i) Significance of the Invention

The significance of this invention lies in the influence, now possible with this invention, of the parasitic, bacterial and viral infection mechanisms controlled by sialic acid, the influence of cell communication and the immune system and the change to the regulation and development mechanisms of human and animal tissues and of tumours. This is achieved by the targeted transfer of sialic acids to biologically relevant glycostructures (glycans, glycan derivatives and glycoconjugates) by means of the trans-sialidases described here.

Resulting from the transfer of the sialic acids to selected carrier structures are, for example, products for changing inflammation reactions, changing cellular interactions in human and animal bodies, protection of the body's own tissues against attacks from one's own immune system (autoimmune reactions), "exposure" of cancer cells in a patient's body so that they can be combatted by the body's own immune system (cancer therapy and cancer prevention), combatting the penetration of pathogenic bacteria into human and animal bodies, prevention of and combatting viral infections, combatting infections of the gastric mucosa by means of *Helicobacter pylori*, combatting newborn meningitis caused by bacteria and viruses, preventive and therapeutic influence of receptors of eucaryotic and procaryotic pathogenic organisms, bacteria, viruses and toxins to prevent the same from becoming active in human and animal bodies, inhibition of the binding of the cholera toxin to human and animal mucosa of the digestive tract, development of a vaccine against Trypanosomiasis, development of enzyme inhibitors to combat (therapy) *Trypanosoma* infections, influence of molecular and cellular identification processes in human and animal bodies, protection of glycoproteins and cells against attack from proteases and other enzymes, amongst other things also for protection against decomposition of the molecules by enzymes of the human and animal digestive tract, influence of the development of body tissues and influence of the morphogenesis of body tissues.

The trans-sialidases in accordance with the invention are characterised by the following DNS and amino acid part sequences as well as by other DNS sequence homologues, eg. with more than 60 percent correspondence (sameness) to these part sequences.

ii) Sequence Details of the Preferred Trans-Sialidases (1) Information for the Enzyme TS1 Sequence:
Features of the DNS of the TS1 part sequence:
length: 1491 base pairs
type: nucleic acid
strand form: double
origin: *Trypanosoma congolense*

```
DNS part sequence of the TS1 enzyme
(SEQ ID NO: 1):
5' ACCGACACCGTTGCTAAATACAGCACTGACGGTGGGAGAACGTGGAA
GAGGGAGGTTATAATTCCGAATGGTGGTGTGGATGCCCACTACTCCCGCG
TCGTTGATGCCACTGTTGTTGCGAAGGGTAATAACATTTATGTTCTCGTT
GGGCGGTACAATGTCACGCGGGGCTACTGGCACAATAGGAACAACAAGGC
TGGCATAGCCGATTGGGAGCCCTTCGTGTACAAGGGCACGGTGAACGTGG
GCACGAAGGGCAATGCCACTGATGTGTCGATCAGCTGGGAGAGGACTGCA
CTGAAGTCGCTGTACAACTTCCCGGTTTCGGGAAGCCCTGGGACGCAGTT
CCTTGGAGGGGCTGGGGGTGGTGTTGTAACATCCAACGGGACGATTGTGC
TGCCAGTGCAGGCAAGGAACAAGGGCAACCGTGTTGTGAGCATGATCCTG
TACTCGGCTGACGATGGAAAGTCATGGCACTTTGGGAAGGGTGAGGCCGG
TGTAGGCACGTCCGAGGCTGCCCTCACTGAGTGGGACGGCAAGCTGCTGA
TTAGTGCACGATCCGATGGTGGACAGGGCTACCGCATGATATTCGAATCG
AGTGACCTTGGTGCGACGTGGAAAGAGATGCTCAACAGCATCTCCCGCGT
GATTGGCAACTCTCCGGGTCGCAGTGGTCCTGGCAGCTCGAGTGGCTTCA
TCACGGTGACAGTGGAGGGTGTGCCTGTGATGCTGATTACCCACCCGAAG
AACCTTAAGGGCTCGTATTATCGGGACCGTCTGGAGCTGTGGATGACGGA
CGGCAATCGTATGTGGCATGTCGGGCAGGTCTCTGAGGGCGACGATAACA
GCGCTTACAGCTCCCTGCTGTACACTCCGGACGGGGTCCTGTACTGCTTG
CATGAGCAGAACATTGATGAGGTGTACAGCCTCCACCTTGTGCGCCTTGT
GGACGAGCTGAAAAGCATTAAATCAACGGCTGTGGTGTGGAAGGCACAGG
ACGAGCTTCTCCTGGGCAACTGCCTCCCGGGCGATAAATACGATCCCGGG
TGTGACGGCATCCCCACCGCTGGGCTTGCCGGGCTGCTGGTAGGACCCCT
GACGGAGAAGACGTGGCCCGACGCGTATCGGTGCGTGAACGCTGCAACCA
GCGCGCTGTGAGCACTGCTGAAGGGGTGCGGCTGGACGTGGGTGGCGGT
GGCCATGTTGTGTGGCCCGTGAGTGAGCAGGGGCAGGACCAGCGGTATTA
```

```
-continued
CTTTACCAACAGCGAGTTCACGCTCGCCGTCACGGTGCGGTTTGACGAGA
TGCCACGGGGGAGCTCCCGTTGCTGGGGTTTGTGAACCGCAAAGGGAAG
GTGAAGAAGATACTGAAGGTGTCGCTGAGCGGGGTGGAGTGGCTCCTGGC
ATACGGGAATGAGTACAACAGCACAGCCGCTGAGCCGCTGGACGTGAACG
AGAGCCACCAGGTGGTGCTAGCGGTTCACGACGGGATGGTCTCC 3'

Amino acid part sequence of the TS1 enzyme
(SEQ ID NO: 2):
TDTVAKYSTDGGRTWKREVIIPNGRVDAHYSRVVDPTVVAKGNNIYVLVG
RYNVTRGYWHNRNNKAGIADWEPFVYKGTVNVGTKGNATDVSISWERTAL
KSLYNFPVSGSPGTQFLGGAGGGVVTSNGTIVLPVQARNKANRVVSMILY
SADDGKSWHFGKGEAGVGTSEAALTEWDGKLLISARSDGGQGYRMIFESS
DLGATWKEMLNSISRVIGNSPGRSGPGSSSGPITVTVEGVPVMLITHPKN
LKGSYYRDRLQLWMTDGNRMWHVGQVSEGDDNSAYSSLLYTPDGVLYCLH
EQNIDEVYSLHLVRLVDELKSIKSTALVWKAQDELLLGNCLPGDKYDPGC
DGIPTAGLAGLLVGPLTEKTWPDAYRCVNAATSGAVSTAEGVRLDVGGGG
HVVWPVSEQGQDQRYYFTNSEFTLAVTVRFDEMPRGELPLLGFVNRKGKV
KKILKVSLSGVEWLLAYGNEYNSTAAEPLDVNESHQVVLALHDGIVS
```

(2) Information for the Sequence of the TS2 Enzyme:
  Features of the DNS of the part sequence of TS2: 831 base pairs
  type: nucleic acid
  strand form: double
  origin: *Trypanosoma congolense*

```
DNS part sequence of the TS2 enzyme
(SEQ ID NO: 3):
5' TTCCGAATTCCCTCACTTGTTGAGATAGACGGCGTGCTTATCGCGAC
ATTCGATACACGTTATCTTCGCGCTTCCGACAGCAGTGTCATAGACACAG
CTATGAAATACAGTGCCGATCAGGGGAAGACGTGGAAAACTGAAATCATA
ATAAAAAATGCTAGACTAACTGATAACTTTTCCCGCGTCGTTGATCCAAC
GGTTGTTGTTAAGGGTGATAACTTGTTTATTTTTGTTGGGAGGTACAAGA
CCTCATCTGCCCCATGGGTCTGGCAGGAAAACGGTAAAGACTGGGATGTA
CTGTTGTACAAGGCCAAGGTGAGGAAGGAATCAGCGGGTGGGGTAGCATC
AGTGAGCTTTACATGGGACGAACCCCTATACCTGAAGCATCTGCTCACCT
CTGTCGGTAAAATAGACGGCAGGTCCCTCATACAATACATTGGTGGCGTT
GGAAATGGTATTGTAACACCGAAAGGTACTATCGTGTTTCCAGTTCAGGT
TTTAAACACCAACAAATCCGTCATGAACATGCTTCTGTATTCAAGTAACG
ACGGAAAAACCTGGGAGTTCAGCAAAACTTCCACACCCGCGGGCACAACT
GAGGCCTCCCTTGTTTGGTGGGATGGACAACTACTTCTCACAAGCAGAAC
AACTCCGGATGTCGGCAGCCGCAAAGTATATTTAACAAGGGACCTCGGAA
CTTCATGGAATGAAGCGATCGGAAGTATCTCTCGTGTAATTGGTAACTCG
CGGTACCGTAACGATCCTGGGGGGTCAGGTAGCTCAATTGCCATAACTGT
GGAGGGAGTACCGGTGATGCTGATTACCCACCCG 3'

Amino acid part sequence of the TS2 enzyme
(SEQ ID NO: 4):
FRIPSLVEIDGVLIATFDTRYLRASDSSLIDTAMKYSADQGKTWKTEIII
KNARLTDNFSRVVDPTVVVKGDNLFIFVGRYNTSSAPWVWQENGKDWDVL
LYKAKVRKESAGGVPSVSFTWDEPLYLKHLLTSVGKIDGRSLIQYIGGVG
NGIVTPKGTIVFPVQVLNTNKSVMNMLLYSSNDGKTWEFSKTSTPAGTTE
ASLVWWDGQLLLTSRTTPDVGSRKVYLTSDLGTSWNEAIGSISRVIGNSR
YRNDPGGSGSSIAITVEGVPVMLITHP
```

The part sequences of the amino acids from enzyme TS1 and enzyme TS2 have a correspondence (sameness) of just approx. 50%. The part sequences therefore clearly characterise two different materials (see FIG. 1).

iii) Description of the Properties of the Newly Found Enzymes TS1 and TS2

A) Physical/Chemical Properties of the Materials

TABLE 1

Basic data for the two trans-sialidases TS1 and TS2

| Properties | TS1 | TS2 |
|---|---|---|
| Temperature optimum | 30-40° C. | 30-40° C. |
| pH optimum | pH 6.5-8.5 | pH 6.5-8.5 |

TABLE 1-continued

Basic data for the two trans-sialidases TS1 and TS2

| Properties | TS1 | TS2 |
|---|---|---|
| Isoelectric point | pH 4-5 | pH 5-6 |
| Molecular weight, native | 400-600 kDa | 120-180 kDa |
| Molecular weight in the reducing SDS page | 90 kDa | 90 kDa |
| Salt effect | 1M KCl and NaCl reduces the activity of both enzymes by 50%, de-salting produces enzyme activity again | |
| Effect of metal ions | 20 mM $Ca^{2+}$, $Mg^{2+}$, $Mn^{2+}$: no effect 5 mM $Cu^{2+}$, $Zn^{2+}$, $Fe^{2+}$, $Co^{2+}$: little effect | |
| Effect of putative inhibitors | 10 mM N-(4-nitrophenyl)oxamic acid: little inhibition 10 mM N-acetyl-2,3-didehydro-2-deoxyneuraminic acid: little inhibition. | | b) Biological Properties of the Materials

The two materials dealt with here are two enzymes which transfer the sialic acids from a donor molecule onto an acceptor molecule.

With both enzymes, sialic acids bonded to glycans, eg. to oligosaccharides, polysaccharides, polysialic acids, glycoproteins and glycolipids act as donors. Of the glycoproteins, in particular lactoferrins (from humans, cows, goats, sheep, horses, camels and other animals), glycolysated whey proteins (from humans, cows, goats, sheep, horses, camels and other animals) and caseins (from humans, cows, goats, sheep, horses, camels and other animals), other glycolysated proteins of human, animal and plant origin, and parts of the same, such as eg. sections from caseins (from humans, cows, goats, sheep, horses, camels and other animals) such as, for example, the glycomacropeptide from the caseins of these animals, are good donors for sialic acids which can be transferred from the enzymes. Gangliosides can also be used as donors.

Both trans-sialidases have a good acceptor specificity for galactooligosaccharides, in particular for beta-galacto-oligosaccharides, such as eg. Vivinal GOS made by the company Borculo Domo Ingredients (BDI) and Oligomate 55 made by the company Yakult. Otherwise, lactitol, lactobionic acid, methyl-β-lactoside, acetyllactosamines, galactopyranosides, trans-galactooligosaccharides, polygalactoses and other glycoconjugates with terminally bonded β(1-3) or β(1-4)-galactose can act as acceptors. A methylation of the galactose residue leads to a reduction of the acceptor function. The methylation of a glucose residue (eg. with the lactose) has a small effect upon the acceptor function. The monosaccharide galactose also serves as an acceptor, even with lower specificity.

The TS1 enzyme shows approximately double the efficiency in transferring the sialic acids onto the corresponding acceptors than does the TS2 enzyme. The substrates can be bonded freely, ie. solubly, or also cell membrane bonded.

The transfer of alpha-2,3-bonded terminal sialic acids onto beta-1,4-bonded terminal galactose residues is also known with the trans-sialidases of *Trypanosoma cruzi* (Schenkman et al., 1991; Vadekerckhove et al., 1992; Scudder et al., 1993) and *Trypanosoma brucei* (Engstler et al., 1992, 1993, 1995). Due to different DNS and amino acid sequences, TS1 and TS2 are, however, different from the already known enzymes. TS1 and TS2 are therefore clearly characterised as novel materials (trans-sialidases). For further differentiation, see the next paragraph.

iv) Differentiation of the Invention from Other Trans-Sialidases, Sialidases and Sialyltransferases An enzyme "trans-sialidase" was described for the first time in the American trypanosome type *Trypanosoma cruzi* (Schenkmann et al., 1991). A short while after, the enzyme could also be demonstrated in the African types *Trypanosoma brucei gambiense*, *Trypanosoma brucei rhodesiense* and *Trypanosoma brucei brucei* (Engstler et al., 1993, Pontes de Carvalho et al., 1993, Engstler et al., 1995). Moreover, trans-sialidase was detected in *Endotrypanum* types (parasites which afflict the sloth) (Medina-Acosta et al., 1994), in *Corynebacterium diphtheriae* (Mattos-Guaraldi et al., 1998) and in the human plasma (Tertov et al., 2001). The so-called sialidases were already known well before the trans-sialidases were demonstrated. These are glycohydrolases which transfer sialic acids from a donor molecule exclusively to water, and so dehydrolyse sialic acids from oligosaccharides and glycoconjugates.

Furthermore, certain enzymes with cytidine monophosphate (CMP)-activated sialic acids can transfer to other sugar residues, mainly galactose and N-acetylgalactosamine. These enzymes are called sialyltransferases (see FIG. 2).

The trans-sialidases in question here do not exclusively transfer sialic acids from a donor molecule to water as do the pure sialidases. However, if there is no suitable acceptor, the trans-sialidases in question here hydrolate the sialic acids just like the basic sialidases. The trans-sialidases in question here do not require any activated sialic acids either for their transfer reaction as do the previously mentioned sialyltransferases. The trans-sialidases also have a broader donor and acceptor specificity than the sialyl transferases and so can be used in a particularly wide variety of manners. The trans-sialidases in question here are therefore more beneficial for industrial utilisation than are the pure sialidases and sialyltransferases.

Figure 3:
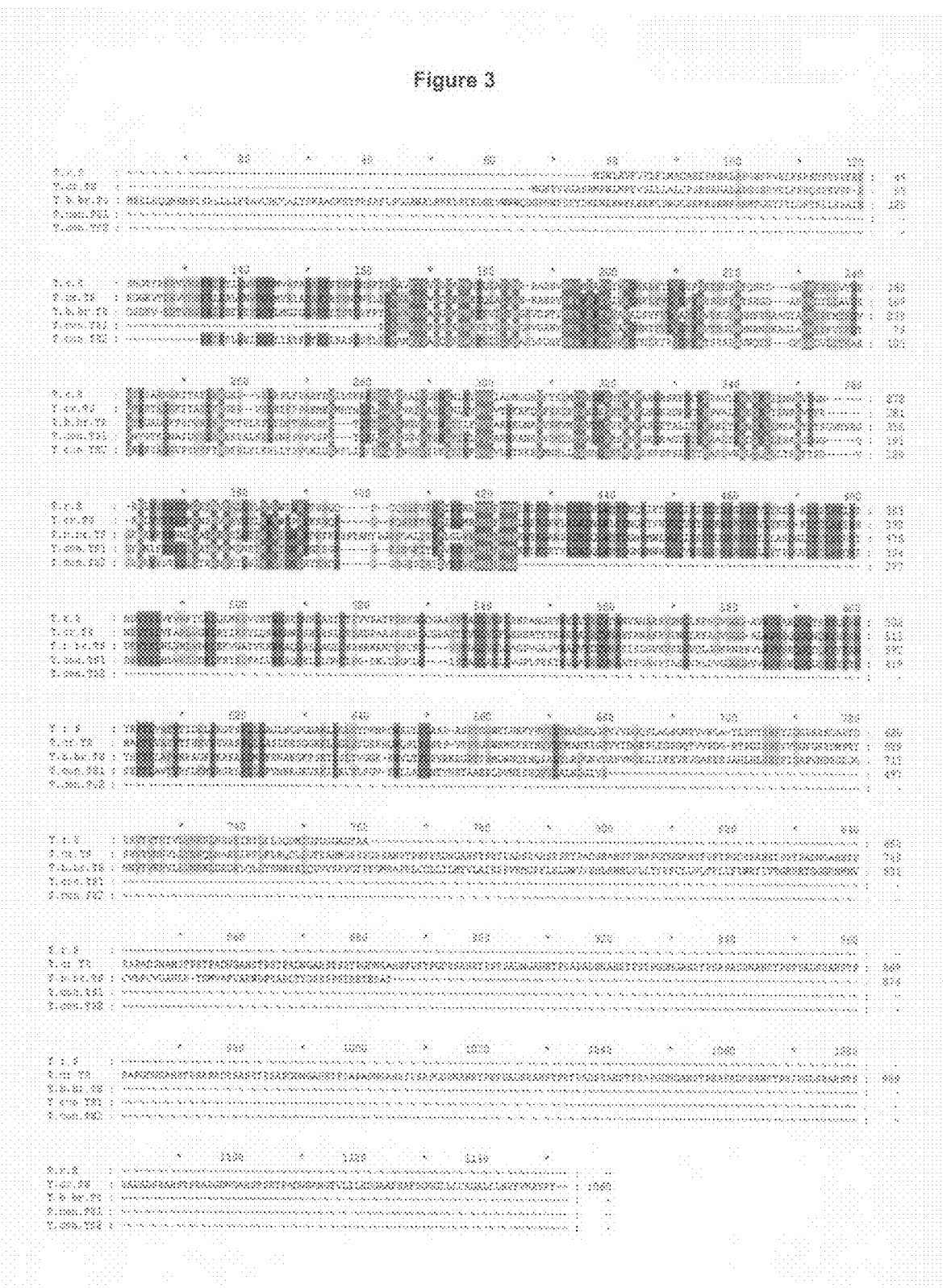
FIG. 3 shows a comparison of the amino acid sequence of the sialidase obtained from *Trypanosoma rangeli* (T.r.s), the trans-sialidase from *Trypanosoma cruzi* (T. cr. TS) and the trans-sialidase from *Trypanosoma brucei brucei* T. b. br. TS) with part sequences of both trans-sialidases from *Trypanosoma congelense* T. con. TS1 (SEQ ID NO. 2) and T. con. TS2 (SEQ ID NO. 4)) in accordance with the invention. Amino acids, which are identical in all sequences, are shown as white on a dark grey background. Amino acids which are identical in at least 4 of the 5 sequences are printed in black on dark grey, whereas amino acids which correspond in at least 3 of the 5 sequences are shown by a lighter grey.

Up till now, only the DNS and amino acid sequences of the trans-sialidases of *Trypanosoma cruzi* and *Trypanosoma brucei brucei* were known, as well as the DNS and amino acid sequence of a pure sialidase from *Trypanosoma rangeli*. The TS1 enzyme in question here has a correspondence (sameness) of less than 60% to the corresponding amino acid part sequence of the trans-sialidase from *Trypanosoma brucei brucei* and a correspondence of less than 50% to the corresponding part sequence of *Trypanosoma cruzi*. The TS2 enzyme in question here has a correspondence (sameness) of less than 50% to the corresponding amino acid part sequence of the trans-sialidase from *Trypanosoma brucei brucei* and a correspondence also of less than 50% to the corresponding part sequence of *Trypanosoma cruzi* (see FIG. 3). Furthermore, it is known that the correspondence of the amino acids between the trans-sialidases of Trypanosomes and the known sialidases and trans-sialidases of bacteria and viruses is only 20% to 30% (Chuenkova et al., 1999, Montagna et al., 2002).

The enzymes described here are therefore newly characterised materials (enzymes), the correspondence (sameness) of which to the corresponding DNS and amino acid sequences of other known enzymes of similar function is less than 60%.

v) Further Comments on this Invention

A) Polypeptides and Functional Equivalents

"Polypeptides" in the sense of the invention include characteristic part-fragments of the amino acid sequences in accordance with the invention as well as amino acid sequences of the enzymes in accordance with the invention and the functional equivalents of the same.

Also included, therefore, in accordance with the invention are "functional equivalents" or "homologues" of the precisely disclosed new polypeptides and enzymes.

"Functional equivalents" or analogues of the precisely disclosed polypeptides within the framework of this invention are polypeptides different to these which, moreover, have the desired biological activity in accordance with the above definition (such as eg. substrate specificity).

"Functional equivalents" should be understood in accordance with the invention as being, in particular, mutants which in at least one of the sequence positions specified above have an amino acid other than that precisely specified but which despite this have one of the biological activities specified here. "Functional equivalents" therefore include the mutants which can be obtained by means of one or more amino acid additions, substituents, deletions and/or inversions, whereby the changes specified can occur in any sequence position as long as they lead to a mutant with the property profile in accordance with the invention. Functional equivalence is therefore in particular also present if the reactivity pattern between the mutants and unchanged polypeptide correspond qualitatively, ie for example the same substrates are changed with different speed.

"Functional equivalents" in the above sense are also precursors of the polypeptides described and functional derivatives and salts of the polypeptides. The term "salts" is understood as salts from carboxyl groups and also acid addition salts of amino groups of the protein molecules in accordance with the invention. Salts of carboxyl groups can be produced in the established manner and comprise inorganic salts, such as for example sodium, calcium, ammonium, iron and zinc salts as well as salts with organic bases, such as for example amines such as triethanol amine, arginine, lysine, piperidine and similar. Acid addition salts, such as for example salts with mineral acids, such as hydrochloric acid or sulphuric acid and salts with organic acids, such as acetic acid and oxalic acid are also included in the subject matter of the invention.

"Functional derivatives" of polypeptides in accordance with the invention can also be produced on functional amino acid side groups or on the N- or C-terminal end of the same with the help of the established techniques. This type of derivative includes, for example, aliphatic esters of carboxylic acid groups, amides of carboxylic acid groups, obtainable by conversion with ammoniac or with a primary or secondary amine; N-acyl derivatives of free amino groups, produced by conversion with acyl groups; or O-acyl derivatives of free hydroxy groups, produced by conversion with acyl groups.

Of course, "functional equivalents" also include polypeptides which are accessible from other organisms and naturally occurring variants. For example, by sequence comparison areas of homologous sequence regions can be established and equivalent enzymes determined according to the precise details of the invention.

"Functional equivalents" also include fragments, prerably individual domains or sequence motives, of the polypeptides in accordance with the invention which eg. have the desired biological function.

Furthermore, "functional equivalents" are fusion proteins which have one of the above-specified polypeptide sequences or functional equivalents derived from the same and at least one other, functionally different, heterologous sequence in functional N- or C-terminal connection (ie. without the fusion protein parts having any substantially adverse functional effect upon one another). Non-limiting examples of this type of heterologous sequence are eg. signal peptides, enzymes, immunoglobulins, surface antigens, receptors or receptor ligands.

"Functional equivalents" of trans-sialidases in accordance with the invention are in particular enzymes the amino acid sequences or part sequences of which have a sequence sameness (sequence homology) of at least 60%, in particular 65% or at least 70%, such as eg. 75%, 80%, 85%, 90%, 95%, 98% or 99% to the corresponding amino acid sequence or part sequence in accordance with SEQ ID NO: 2 or 4, calculated using the algorithm of Pearson and Lipman, Proc. Natl. Acad, Sci, (USA) 85(8), 1988, 2444-2448.

In the case of a possible protein glycosylation, equivalents in accordance with the invention include proteins of the type indicated above in deglycosylated or glycosylated form and modified forms obtained by a change to the glycosylation pattern.

Homologues of the proteins or polypeptides in accordance with the invention can be produced by mutagenesis, eg. by point mutation, lengthening or shortening of the protein. The term "homologue" as used here also relates to a variant form of the protein which acts as an agonist or antagonist of the protein activity.

Homologues of the proteins in accordance with the invention can be identified by screening of combinatory banks of mutants, such as eg. shortening mutants. For example, a variegated bank of protein variants can be produced by combinatory mutagenesis on the nucleic acid level, such as eg. by enzymatic ligation of a mixture of synthetic oligonucleotides. There are a number of methods which can be used for the production of banks of potential homologues from a degenerated oligonucleotide sequence. The chemical synthesis of a degenerated gene sequence can by carried out in a DNA synthesis machine, and the synthetic gene can then be ligated into an appropriate expression vector. The use of a degenerated gene set makes it possible to provide all sequences in one mixture which code the desired set to potential protein sequences. Methods for the synthesis of degenerated oligonucleotides are known to experts in the field (eg. Narang, S. A. (1983) Tetrahedron 39:3; Itakura et al. (1984) Annu. Rev. Biochem. 52:323; Itakura et al., (1984) Science 198:1056; Ike et al. (1983) Nucleic Acids Res. 11:477).

b) Polynucleotides

"Polynucleotides" in the sense of this invention include characteristic part fragments of the nucleic acid sequences in accordance with the invention which code for amino acid part sequences of enzymes in accordance with the invention, and also nucleic acid sequences which code for enzymes and the functional equivalents of the same. Polynucleotides preferably comprise more than approximately 20, and in particular more than approximately 30, such as eg. more than approximately 45 or more than approximately 60 nucleic acid residues.

"Oligonucleotides" include in particular a sequence of less than approximately 60, preferably less than approximately 45, in particular less than approximately 30 or less then approximately 20 nucleic acid residues.

All "nucleic acid sequences" mentioned here can be produced in a conventional manner by means of chemical synthesis from the nucleotide building blocks, for example by means of fragment condensation of individual overlapping, complementary nucleic acid building blocks of the double helix. The chemical synthesis of oligonucleotides can take place, for example, in the established manner, in accordance with the phosphoamidite method (Voet, Voet, $2^{nd}$ Edition, Wiley Press New York, pages 896-897). The attachment of synthetic oligonucleotides and filling of gaps with the help of the Klenow fragment of the DNA polymerase, ligation reactions and general cloning methods are described in Sambrook et al. (1989), Molecular Cloning: A laboratory manual, Cold Spring Harbor Laboratory Press.

The subject matter of the invention also includes nucleic acid sequences (single- and double-stranded DNA and RNA sequences, such as eg. cDNA and mRNA), coding for one of the above polypeptides and the functional equivalents of the same, which eg. are also accessible using synthetic nucleotide analogues.

The invention relates to isolated nucleic acid molecules which code for polypeptides or proteins in accordance with the invention, or biologically active sections of the same as well as to nucleic acid fragments which can be used eg. as hybridisation probes or primers for the identification or amplification of coding nucleic acids in accordance with the invention.

The nucleic acid molecules in accordance with the invention can in addition contain untranslated sequences of the 3' and/or 5' end of the coding gene range.

An "isolated" nucleic acid molecule is separated from other nucleic acid molecules which are present in the natural source of the nucleic acid and can moreover be substantially free from any other cellular material or culture medium if it is produced by recombinant techniques or be free from chemical pre-stages or other chemicals if it is chemically synthesised.

A nucleic acid molecule in accordance with the invention can be isolated by means of molecular biological standard techniques and the sequence information provided in accordance with the invention. For example, cDNA can be isolated from a suitable cDNA bank whereby one of the precisely disclosed full sequences or a section of the same are used as hybridisation probes and standard hybridisation techniques (as eg. described in Sambrook, J., Fritsch, E. F. and Maniatis, T. Molecular Cloning: A Laboratory Manual, $2^{nd}$ Edition, Cold Spring Harbor Laboratory, Cold Spring Harbor Laboratory Press, Cold Spring Harbor, N.Y., 1989). Moreover, a nucleic acid molecule, comprising one of the disclosed sequences or a section of the same, can be isolated by polymerase chain reaction, whereby the oligonucleotide primers which were created on the basis of this sequence, are used. The nucleic acid amplified in this way can be cloned in a suitable vector and be characterised by DNA sequence analysis. The oligonucleotides in accordance with the invention can also by produced by standard synthesis methods, eg. with an automatic DNA synthesis unit.

The invention further comprises the "complementary" nucleic acid molecules of the precisely described nucleotide sequences, or a section of the same.

The nucleotide sequences in accordance with the invention make it possible to produce probes and primers which can be used to identify and/or clone homologous sequences in other cell-types and organisms. This type of probe and primer usually comprises a nucleotide sequence range which, under stringent conditions, hybridises to at least approximately 12, preferably at least approximately 25, such as eg. approximately 40, 50 or 75 subsequent nucleotides of a sense strand of a nucleic acid sequence in accordance with the invention or of a corresponding antisense strand.

Further nucleic acid sequences in accordance with the invention are derived from SEQ ID NO: 1 and 3 and differ from this by the addition, substitution, insertion or deletion of individual or several nucleotides, but code, moreover, for polypeptides with the desired property profile.

The invention also includes those nucleic acid sequences which comprise so-called dumb mutations or which are changed in comparison to a precisely specified sequence according to the codon use of a special origin or host organism, as well as naturally occurring variants such as eg. splice variants or allele variants of the same. The subject matter also includes sequences obtained by means of conservative nucleotide substitutions (ie. the amino acid in question is replaced by an aimo acid with the same charge, size, polarity and/or solubility).

The subject matter of the invention also includes the molecules derived from the precisely disclosed nucleic acids by means of sequence polymorphisms. These genetic polymorphisms can exist between individuals within a population due to the natural variation. These natural variations generally bring about a variance of 1 to 5% in the nucleotide sequence of a gene.

Furthermore, the invention also includes nucleic acid sequences which hybridise with the above-specified coding sequences or are complementary to the same. These polynucleotides can be located by the sampling of genomic or cDNA banks and, if so required, can be propagated from here using appropriate primers by means of PCR, and can then, for example, be isolated with suitable probes. Another possibility offers the transformation of suitable microorganisms with polynucleotides or vectors in accordance with the invention, the propagation of the microorganisms and so of the polynucleotides and their subsequent isolation. Moreover, polynucleotides in accordance with the invention can also be synthesised by chemical means.

The property of being able to "hybridise" to polynucleotides is to be understood as the capability of a poly- or oligonucleotide to bind to a nearly complementary sequence under stringent conditions, whereas, under these conditions, non-specific bonds between non-complementary partners do not occur. For this, the sequences should be 70-100% complementary, and preferably 90-100%. The property of complementary sequences being able to bind to one another specifically is put to use, for example, in the Northern or Southern blot technique or with primer binding in PCR or RT PCR. Generally, oligonucleotides with a length of at least 30 base pairs are used for this.

"Stringent" conditions are to be understand as when, for example, following the Southern or Northern Blot, the DNA or RNA fragments are hybridised on the membranes with a probe under specific conditions, ie. with a temperature of 60-70° C. (38-42° C. with 50% hybridisation solutions which contain 50% formamide). Moreover, the conditions are specific or stringent when the washing steps carried out following on from the hybridisation for the elution of non-specifically hybridised DNA or RNA probes are also specifically carried out. Specific washing steps are generally the washing, twice over, at 20-25° C. for 5-10 mins with 2×SSC buffer which contains 0.1% SDS (sodium dodecylsulphate) and subsequent washing, twice over, with a buffer with low ionic strength (eg. 0.1×SSC with 0.1% SDS) at a higher temperature (eg. 64° C.). [20×: 3M NaCl, 0.3 M sodium citrate, pH 7.0]. In so doing, only those nucleic acids which are complementary to a large extent remain bonded to one another. The creation of stringent conditions is known to experts in the field and is described eg. in Ausubel et al., Current Protocols in Molecular Biology, John Wiley & Sons, N.Y. (1989), 6.3.1-6.3.6.

A further aspect of the invention relates to "antisense" nucleic acids. These include a nucleotide sequence which is complementary to a coding "sense" nucleic acid. The antisense nucleic acid can be complementary to the whole coding strand or to just a section of the same. With a further embodiment, the antisense nucleic acid molecule is antisense to a non-coding region of the coding strand of a nucleotide sequence. The term "non-coding region" relates to the sequence sections identified as 5' and 3' untranslated regions.

An antisense oligonucleotide can be eg. approximately 5, 10, 15, 20, 25, 30, 35, 40, 45 or 50 nucleotides long. An antisense nucleic acid in accordance with the invention can be constructed by means of chemical synthesis and enzymatic ligation reactions using methods established in this specialist area. An antisense nucleic acid can be chemically synthesised, whereby naturally occurring nucleotides or differently modified nucleotides are used if they are of such a form that they increase the biological stability of the molecules or increase the physical stability of the duplex which has emerged between the antisense and sense nucleic acid. For example, phosphorthioate derivatives and acridine substituted nucleotides are used. Examples of modified nucleotides which can be used in order to create antisense nucleic acid are eg. 5-fluorouracil, 5-bromouracil, 5-chlorouracil, 5-iodouracil, hypoxanthin, xanthin, 4-acetylcytosin and similar.

The antisense nucleic acid molecules in accordance with the invention are generally administered to a cell or produced in situ so that they hybridise with the cellular mRNA and/or a coding DNA or bind to the same, so that the expression of the protein is inhibitied eg. by inhibition of the transcription and/or translation.

In the context of the invention, the terms "express" or "strengthening" or "over-expression" describe the production or increase of the intracellular activity of one or more enzymes in a micro-organism which are coded by the corresponding DNA. For this, one can, for example, introduce a gene into an organism, replace an existing gene with another gene, increase the copy number of the gene or the genes, use a strong promoter, or use a gene which codes for a corresponding enzyme with high activity, and one can, if so required, combine these measures.

In the context of the invention, the terms "weaken" and "reduce" describe the weakening or the reduction of the intracellular activity of one or more enzymes in a microorganism which can be coded by the corresponding DNA. For this, one can, for example, delete a gene in an organism, replace an existing gene by another gene, lower the copy number of a transcript of the gene or genes, use a weak promoter or use a gene which codes for a corresponding enzyme with a lower activity, and one can, if so required, combine these measures.

c) Expression Constructs and Vectors:

The subject matter of the invention also includes expression constructs, including among the genetic control of regulative nucleic acid sequences a nucleic acid sequence coding for a polypeptide in accordance with the invention; as well as vectors comprising at least one of these expression constructs. Preferably, these constructs in accordance with the invention comprise a promoter 5' upstream from the respective coding sequence and a terminator sequence 3' downstream, and, if required, additional conventional regulative elements, and respectively operatively connected to the coding sequence.

An "operative connection" is understood as the sequential arrangement of promoters, coding sequence, terminator and, if required, further regulative elements of such a type that each of the regulative elements can fulfil its function according to stipulations with the expression of the coding sequence. Examples of operatively connectable sequences are targeting sequences and enhancers, polyadenylation signals and similar. Further regulative elements include selectable markers, amplification signals, replication origins and similar. Suitable regulatory sequences are described eg. in Goeddel, Gene Expression Technology: Methods in Enzymology 185, Academic Press, San Diego, Calif. (1990).

In addition to the artificial regulation sequences, the natural regulation sequence can still be present before the actual structural gene. By means of genetic change, this natural regulation can, if so required, be discarded and the expression of the gene increased or decreased. The gene construct can, however, also be more simply structured, ie. no additional regulation signals are inserted before the structural gene, and the natural promoter with its regulation is not removed. Instead of this, the natural regulation sequence is mutated in such a way that no more regulation takes place, and the gene expression is increased or decreased. The nucleic acid sequences can be contained in one or more copies in the gene construct.

Examples of usable promoters are: cos-, tac-, trp-, tet-, trp-tet-, lpp-, lac-, lpp-lac-, laclq-, T7-, T5-, T3-, gal-, trc-, ara-, SP6-, lambda-PR- or im lambda-PL promoters which are beneficially used in gram-negative bacteria; as well as the gram-positive promotors amy and SP02, the yeast promoters ADC1, MFalpha, AC, P-60, CYC1, GAPDH or the plant promoters Ca MV/35S, SSU, OCS, lib4, usp, STLS1, B33, not or the ubiquitin or phaseolin promoters. Particularly preferred is the use of inducible promoters such as eg. light and in particular temperature inducible promotors such as the $P_rP_l$ promoters. In principle, all natural promoters can be used with their regulation sequences. Furthermore, synthetic promoters can also beneficially be used.

The specified regulatory sequences should make possible the targeted expression of the nucleic acid sequences and the protein expression. This can mean, for example, dependent upon the host organism, that the gene is only expressed or over-expressed following induction, or that it is expressed and/or over-expressed immediately.

The regulatory sequences and factors here can preferably have a positive effect upon and in this way increase or decrease the expression. Strengthening of the regulatory elements can therefore beneficially take place on the transcription level, whereby strong transcription signals such as promoters and/or "enhancers" can be used. Alongside this, however, a strengthening of the translation is also possible, whereby, for example, the stability of the mRNA is improved.

The production of an expression cassette happens by means of fusion of a suitable promoter with a suitable coding nucleotide sequence and a terminator or polyadenylation signal. For this, one uses current recombination and cloning techniques as described, for example in T. Maniatis, E. F. Fritsch and J. Sambrook, Molecular Cloning: A Laboratory Manual, Cold Spring Harbor Laboratory, Cold Spring Harbor, N.Y. (1989) and in T. J. Silhavy, M. L. Berman and L. W. Enquist, Experiments with Gene Fusions, Cold Spring Harbor Laboratory, Cold Spring Harbor, N.Y. (1984) and in Ausubel, F. M. et al., Current Protocols in Molecular Biology, Greene Publishing Assoc. and Wiley Interscience (1987).

For expression in a suitable host organism, the recombinant nucleic acid construct or gene construct is beneficially inserted into a host-specific vector which makes optimal expression of the genes in the host possible.

"Vectors" are well known to experts in the field, and can, for example, be taken from "Cloning Vectors" (Pouwels P. H. et al., Hrsg, Elsevier, Amsterdam-N.Y.-Oxford, 1985). As well as plasmids, vectors are also to be understood as being all other vectors known to experts in the field, such as, for example, phages, viruses such as SV40, CMV, baculovirus and adenovirus, transposons, IS elements, phasmids, cosmids and linear or circular DNA. These vectors can be autonomously replicated in the host organism or chromosomally replicated.

The following can be specified as examples of suitable expression vectors:

Common fusion expression vectors, such as pGEX (Pharmacia Biotech Inc; Smith, D. B. and Johnson, K. S. (1988) Gene 67:31-40), pMAL (New England Biolabs, Beverly, Mass.) and pRIT 5 (Pharmacia, Piscataway, N.J.) with which glutathione-5-transferase (GST), maltose E-binding protein or protein A is fusioned to the recombinant target protein.

Non-fusion protein expression vectors such as pTrc (Amann et al., (1988) Gene 69:310-315) and pET 11d (Studier et al. Gene Expression Technology: Methods in Enzymology 185, Academic Press, San Diego, Calif. (1990) 60-89).

Yeast expression vectors for expression in the yeast *S. cerevisiae*, such as pYepSec1 (Baldari et al., (1987) Embo J. 6:229-234), pMFa (Kurjan and Herskowitz (1982) Cell 30:933-943), pJRY88 (Schultz et al. (1987) gene 54:113-123) and pYES2 (Invitrogen Corporation, San Diego, Calif.). Vectors and methods for the construction of vectors which are suitable for use in other fungi, such as filamentous fungi, include those which are described in detail in: van den Hondel, C.A.M.J.J. & Punt, P. J. (1991) "Gene transfer systems and vector development for filamentous fungi, in: Applied Molecular Genetics of Fungi, J. F. Peberdy et al., Hrsg., pages 1-28, Cambridge University Press: Cambridge.

Baculovirus vectors which are available for the expression of proteins in cultured insect cells (for example Sf9 cells) include the pAc array (Smith et al., (1983) Mol. Cell Biol. 3:2156-2165) and the pVL array (Lucklow and Summers (1989) Virology 170:31-39).

Plant expression vectors such as those which are described in detail in: Becker, D., Kemper, E., Schell, J. and Masterson, R. (1992) "New plant binary vectors with selectable markers located proximal to the left border", Plant Mol. Biol. 20:1195-1197; and Bevan, M. W. (1984) "Binary *Agrobacterium* vectors for plant transformation", Nucl. Acids Res. 12:8711-8721.

Mammal expression vectors such as pCDM8 (Seed, B. (1987) Nature 329:840) and pMT2PC (Kaufman et al., (1987) EMBO J. 6:187-195).

Other suitable expression systems for procaryontic and eucaryotic cells are described in chapters 16 and 17 of Sambrook, J., Fritsch, E. F. and Maniatis, T., Molecular cloning: A Laboratory Manual, $2^{nd}$ Edition, Cold Spring Harbor Laboratory, Cold Spring Harbor Laboratory Press, Cold Spring Harbor, N.Y., 1989.

d) Recombinant Microorganisms:

With the help of the vectors in accordance with the invention, recombinant microorganisms can be produced which, for example, are transformed with at least one vector in accordance with the invention and can be used for the production of the polypeptides in accordance with the invention. The recombinant constructs in accordance with the invention described above are beneficially introduced to and expressed in a suitable host system. For this, commonly used cloning and transfection methods known to experts in the field are preferably used, such as for example coprecipitation, protoplast fusion, electroporation, retroviral transfection and similar so as to bring the specified nucleic acids in the respective expression system to expression. Suitable systems are described, for example, in Current Protocols in Molecular Biology, F. Ausubel et al., Hrsg., Wiley Interscience, New York 1997 or Sambrook et al. Molecular Cloning: A Laboratory Manual, 2$^{nd}$ Edition, Cold Spring Harbor Laboratory, Cold Spring Harbor Laboratory Press, Cold Spring Harbor, N.Y., 1989.

In accordance with the invention, homologously recombined microorganisms can also be produced. For this, a vector is produced which contains at least one section of a gene in accordance with the invention or of a coding sequence into which, if so required, at least one amino acid deletion, addition or substitution is introduced in order to change the sequence in accordance with the invention, eg. to disrupt it functionally ("knockout" vector). The sequence introduced can eg. also be a homologue from a related microorganism or be derived from a mammal, yeast or insect source. The vector used for the homologous recombination can alternatively be of such a form that the endogenous gene is mutated or changed in another way in the homologous recombination, but still codes the functional protein (eg. the regulatory region located upstream can be changed in such a way that in this way, the expression of the endogenous protein is changed). The changed section of the gene in accordance with the invention is in the homologous recombination vector. The construction of suitable vectors for the homologous recombination is described eg. in Thomas, K. R. and Capecchi, M. R. (1987) Cell 51:503.

As host organisms, in principle all organisms are suitable which make possible an expression of the nucleic acids in accordance with the invention, of their allele variants, their functional equivalents or derivatives. Host organisms are to be understood as being, for example, bacteria, fungi, yeasts, plant or animal cells. Preferred organisms are bacteria, such as those of the *Escherichia* genus such as eg. *Escherichia coli, Streptomyces, Bacilius* or *Pseudomonas*, eucaryotic microorganisms such as *Saccharomyces cerevisiae, Aspergillus*, higher eucaryotic cells from animals or plants, for example Sf9 or CHO cells.

As host organisms, in principle all organisms are suitable which make possible an expression of the nucleic acids in accordance with the invention, of their allele variants, their functional equivalents or derivatives. Host organisms are to be understood as being, for example, bacteria, fungi, yeasts, plant or animal cells. Preferred organisms are bacteria, such as those of the *Escherichia* genus such as eg. *Escherichia coli, Streptomyces, Bacilius* or *Pseudomonas*, eucaryotic microorganisms such as *Saccharomyces cerevisiae, Aspergillus*, higher eucaryotic cells from animals or plants, for example Sf9 or CHO cells.

The selection of successfully transformed organisms can take place using marker genes which are also contained in the vector or in the expression cassette. Examples of this type of marker gene are genes for antibiotic resistance and for enzymes which catalyse a colour-giving reaction which brings about a colouring of the transformed cell. These can then be selected by means of automatic cell sorting. Microorganisms successfully transformed with a vector and which carry a corresponding antibiotic resistance gene (eg. G418 or hygromycin) can be selected by corresponding media containing antibiotics or agars. Marker proteins which are presented on the surface of the cell can be used for selection by means of affinity chromatography.

The combination of the host organisms and the vectors suitable for the organisms such as plasmids, viruses or phages, such as for example plasmids with the RNA polymerase/promoter system, the phages 8 or 7 or other temperent phages or transposons and/or other beneficial regulatory sequences, forms an expression system. The term "expression system" should be understood, for example, as the combination of mammalian cells, such as CHO cells and vectors, such as pcDNA3neo vectors which are suitable for mammalian cells.

If so desired, the gene product can also be introduced for expression to transgenic organisms such as transgenic animals, in particular mice, sheep or transgenic plants.

e) Recombinant Production of Polypeptides:

Furthermore, the subject matter of the invention includes methods for the recombinant production of a polypeptide in accordance with the invention or of functional, biologically active fragments of the same, whereby one cultivates a polypeptide-producing microorganism, if required induces the expression of the polypeptides, and isolates this from the culture. The polypeptides can in this way also be produced on a large technical scale if so desired.

The recombinant microorganism can be cultivated and fermented in accordance with known methods. Bacteria can, for example, be propagated in TB or LB medium and at a temperature of 20 to 40° C. and with a pH value of 6 to 9. Suitable cultivation conditions are described in detail, for example, in T. Maniatis, E. F. Fritsch and J. Sambrook, Molecular Cloning: A Laboratory Manual, Cold Spring Harbor Laboratory, Cold Spring Harbor, N.Y. (1989).

If the polypeptides are not separated in the culture medium, the cells are then broken up and the product obtained from the lysate in accordance with the known protein isolation methods. If so chosen, the cells can be broken up by means of high-frequency ultrasound, by high pressure, such as eg. in a French pressure cell, by osmolysis, by the effect of detergents, lytic enzymes or organic solvents, by homogenizators or by a combination of several of the methods listed.

Purification of the polypeptides can be achieved using known, chromatographic methods, such as molecular sieve chromatography (gel filtration), such as Q-Sepharose chromatography, ion exchange chromatography and hydrophobic chromatography, as well as using other conventional methods such as ultrafiltration, crystallisation, salting out, dialysis and native gel electrophoresis. Suitable methods are described, for example, in Cooper, F. G., Biochemical Working Methods, Verlag Walter de Gruyter, Berlin, N.Y. or in Scopes, R., Protein purification, Springer Verlag, New York, Heidelberg, Berlin. The same applies for non-recombinantly produced polypeptides.

For the isolation of the recombinant protein, it is particularly beneficial to use vector systems or oligonucleotides which lengthen the cDNA by certain nucleotide sequences and so code for changed polypeptides or fusion proteins which eg. contribute to simpler purification. This type of suitable modification can be, for example, so-called "tags" acting as anchors such as eg. the modification known as the hexa-histidine anchor or epitopes which can be identified as antigens of antibodies (described, for example, in Harlow, E. and Lane, D., 1988, Antibodies: A Laboratory Manual. Cold Spring Harbor (N.Y.) Press). These anchors can serve to attach the proteins onto a solid carrier such as, eg. a polymer matrix which, for example, can be filled in a chromatography column, or can be used on a microtiter plate or on some other carrier.

At the same time, these anchors can also be used for the identification of the proteins. For the identification of the proteins, conventional markers, such as fluorescent dyes, enzyme markers which after the reaction with a substrate form a detectable reaction product, or radioactive markers, on their own or in combination with the anchors for derivatisation of the proteins, can also be used.

f) Purification of the Desired Sialization Product from the Culture

The desired product can be obtained from the microorganism or from the culture supernatant by means of different methods known within the specialist field. If the desired product is not separated from the cells, the cells can be harvested from the culture by slow centrifugation, the cells can be lysed by standard techniques such as mechanical force or ultrasound treatment. The cell detritus is removed by centrifugation, and the supernatant fraction which contains the soluble proteins, is obtained for the further purification of the desired compound. If the product is separated from the cells, the cells are removed from the culture by means of slow centrifugation, and the supernatant fraction is kept for further purification.

The supernatant fraction from both purification processes can be subjected to chromatography with a suitable resin whereby the desired molecule with higher selectivity than the impurities is either withheld on the chromatography resin or passes this. These chromatography steps can, if necessary, be repeated, whereby the same or other chromatography resins are used. An expert in the field is proficient in the selection of the suitable chromatography resins and the most effective application of the same for a specific molecule to be purified. The purified product can be concentrated by filtration or ultrafiltration and kept at a temperature at which the stability of the product is maximal.

Many purification methods are known from the prior art. These purification techniques are described eg. in Bailey, J. E. & Ollis, D. F. Biochemical Engineering Fundamentals, McGraw-Hill: New York (1986).

The identify and purity of the isolated compounds can be determined by techniques from the prior art. These include high performance liquid chromatography (HPLC), spectroscopic processes, colouring processes, thin layer chromatography, NIRS, enzyme test or microbiological tests. These analysis methods are summarised, eg. in: Patek et al. (1994) Appl. Environ. Microbiol. 60:133-140; Malakhova et al. (1996) Biotekhnologiya 11 27-32; and Schmidt et al. (1998) Bioprocess Engineer. 19:67-70. Ullmann's Encylopedia of Industrial Chemistry (1996) Bd. A27, VCH: Weinheim, pages 89-90, pages 521-540, pages 540-547, pages 559-566, 575-581 and pages 581-587; Michal, G (1999) Biochemical Pathways: An Atlas of Biochemistry and Molecular Biology, John Wiley and Sons; Fallon, A. et al. (1987) Applications of HPLC in Biochemistry in: Laboratory Techniques in Biochemistry and Molecular Biology, Bd. 17.

The following non-limiting examples describe special embodiments of the invention.

EXAMPLES OF THE PRODUCTION, PURIFICATION AND USE OF THE TRANS-SIALIDASES IN QUESTION HERE

General

The cloning steps carried out within the framework of this invention such as eg. restriction splitting, agarose gel electrophoresis, purification of DNA fragments, transfer of nucleic acids to nitrocellulose and nylon membranes, connection of DNA fragments, transformation of cells, culturing of bacteria, propagation of phages and sequence analysis of recombinant DNA were carried out as described by Sambrook et al. (1989) loc. cit.

Example 1

Isolation of the Enzymes from Cultures of *Trypanosoma congolense*

The procyclical forms of *Trypanosoma congolense* (lodged at the Swiss Tropical Institute Basel (STIB) as stem No. 249) can be cultured at 27° C. without $CO_2$ in SM/SDM 79 medium which contains 10% foetal calf serum and hemin. After three to four days, the number of cells has risen from $1\times10^6$ to approx. $7\times10^6$/ml, and the culture supernatant is separated by centrifugation, filtered and concentrated by ultrafiltration. In the culture supernatant obtained in this way, 84% of the enzyme activity can be observed, whereas another 16% of the enzyme activity can be detected bonded to the cell pellet. The concentrated culture supernatants are directly used as enzyme concentrate for the trans-sialidase reactions. The desired sialated molecules are isolated from the culture supernatant after the reaction.

Example 2

Purification of the Enzymes

For the isolation of pure enzymes, the concentrated culture supernatant is introduced to an ion exchange column (Q Sepharose). The column is eluated with a salt gradient after washing. TS2 eluates with a salt concentration of max. 0.2M, and TS1 with a salt gradient of min. 0.2M. After elution, both enzymes are separated by means of isoelectric focussing, gel filtration (Sephades G150 SF), affinity chromatography or protein precipitation until purified to apparent homogeneity.

Example 3

Determination of the Enzyme Activity

In order to determine the transfer activity of the trans-sialidase, 25 µl enzyme solution in 50 mM BisTris buffer, pH7.0, are incubated together with 1 mM NeufAc-α(2-3) lactose as a donor and 0.5 mM 4-methylumbelliferyl galactoside as an acceptor in a final volume of 50 µl at 37° C. for 2 hrs. The incubation is halted by adding 1 ml ice cold water. The reaction batch is then introduced to columns previously filled with 0.3 ml Q Sepharose FF (acetate form) and pre-equilibrated with water. After having washed out the acceptor with water and having discarded the dead volume (200 µl 1N HCl), the sialated product is eluated with 1N HCl (700 µl). Following acid hydrolysis of the product at 95° C. for 45 mins and cooling on ice, the probe is neutralised with 250-290 µl 2 N NaOH and 300 µl 1M glycin/NaOH buffer pH 10.0. The fluorescence of the released methylumbelliferone is measured in black 96 well plates (Microfluor, Dynex, U.S.A.) with a stimulation wave length of 365 nm and an emission wave length of 450 nm. The activity of the enzyme corresponds to the intensity of the fluorescence measured and can be read off on a previously established calibration curve (method in accordance with Engstler et al. 1992).

Example 4

Production of Transgenic Production Organisms (Bacteria, Yeasts, Fungi, Plants) for the Enzymes The DNS part sequences of TS1 and TS2 described here for the first time make it possible, by means of routinely used standard techniques, to establish the full DNS sequences of the enzymes (in particular because the DNS sequences presented here do not contain any non-coding introns). The corresponding standard techniques are eg. the "polymerase chain reaction" technique (PCR technique), "Southern blott" using the genomic DNS or cDNA and mRNA techniques which can be carried out with the help of commercially available kits, for example made by the companies Invitrogen or Clontech. The techniques are know to experts in the field and are described, among other places, in: Ausubel et al: Current Protocols in Molecular Biology, Edition 1989 and 2001. The full DNS of the respective enzymes or functional part sequences of the same are introduced by means of standard transformation techniques (Ausubel et al.) into the desired production organisms. The transgenic organisms produce TS1 and TS2, and can be isolated from the transgenic organisms and/or the culture supernatants of the same. As receiver organisms of the DNS which codes TS1 or TS2, procaryontic bacteria, eucaryontic microorganisms, yeasts and other fungi, eucaryontic cell cultures, algae, plants, seeds, animals, parts of animals, tissue, hybridoma, transgenic organisms and gene-biological, gene-therapeutic and transgenic recombinants and organisms, organs, tissues and cells derived from the same, are used. The enzymes in question here can be isolated from the corresponding wholes or parts of transgenic organisms, from their culture supernatants, from organs, tissues, cells, biological liquids, exudates, eyes, blood, lymph, milk, plants, algae and seeds, as well as parts of the same.

Example 5

Reaction Example of the Enzymes 6 kg of glycomacropeptide (GMP) are dissolved together with 1 kg galactooligosaccharide with a chain length of 6-10 sugars in a conventionally used 50 mM BisTris buffer pH 7.0 (eg. made by the company Merk, Darmstadt). The solution is displaced with 1 litre of the culture supernatant of *Trypanosoma congolense* containing trans-sialidase, and incubated at 37° C. for 3 hours. After this period, the trans-sialidase has transferred the sialic acids from the GMP to the galactooligosaccharides. The sialated products can be separated and purified with the help of conventional chromatographic methods (Ausubel et al.) or filter techniques, and are available in pure state for product formulations.

Glycomacropeptide (GMP) is a waste product from cheese production from cows' milk. Following the precipitation of the casein for the cheese preparation, it can be isolated from the remaining whey by means of filter techniques.

Galactooligosaccharides are produced when lactose is converted by means of the commercially available enzyme beta-galactosidase. With this conversion, on the one hand, beta-galactosidase splits the lactose into its monomer sugars. On the other hand, with this conversion, in a side reaction during this conversion, galactooligosaccharides with longer chains also emerge which can be separated and then are available as acceptors for the trans-sialidase reaction.

Example 6

Use of the Enzymes

Both of the isolated enzymes can, for example, be used for the sialization of polymers containing beta-galactose (such as Gum arabicum etc.), and in particular for polylactosamines and galactans, as well as for galactooligosaccharides (GOS), in particular for beta-galactooligosaccharides, such as eg. Vivinal GOS made by the company Borculo Domo Ingredients (BDI) and Oligmate 55 made by the company Yakult.

These polymer galactose sugars and newly formed galactooligosaccharides (production as described in Example 5) can be sialated with the help of the trans-sialidases dealt with in this patent. As donors for the sialic acids, all of the donors mentioned above, and in particular the glycomacropeptide from caseins (from humans, cows, goats, sheep, horses, camels and other animals) can be used. Sialated sugar structures show an increased similarity to acid sugars which can also be found in the human body and have many types of function there.

The invention claimed is:

1. An isolated polynucleotide which encodes for a protein with trans-sialidase activity, wherein said polynucleotide can be isolated from *Trypanosoma congolense* and which comprises one of the nucleic acid sequences selected from the group consisting of SEQ ID NO: 1 and 3; the polynucleotides complementary to the same; or nucleotide sequences differing from said polynucleotides by degeneration of the genetic code.

2. The isolated polynucleotide of claim 1, which encodes for a protein with trans-sialidase activity and catalyzes the transfer of sialic acid from a donor onto an acceptor molecule.

3. An isolated oligonucleotide, which hybridizes with a polynucleotide of claim 1 or 2 under stringent conditions comprising washing at 20-25° C. for 5-10 minutes with 2×SSC buffer containing 0.1% SDS and a subsequent washing with a buffer of 0.1×SSC buffer with 0.1% SDS, at a temperature of 64° C.

4. An isolated polynucleotide, which hybridizes with an oligonucleotide of claim 3 under stringent conditions, comprising washing at 20-25° C. for 5-10 minutes with 2×SSC buffer containing 0.1% SDS and a subsequent washing with a buffer of 0.1×SSC buffer with 0.1% SDS, at a temperature of 64° C., and encodes for a gene product of microorganisms of the *Trypanosoma* genus.

5. An isolated polypeptide, which is encoded by the isolated polynucleotide of claim 1 or 2, wherein the isolated polypeptide is encoded by the nucleic acid sequence consisting of SEQ ID NO: 1 or 3.

6. The isolated polynucleotide of claim 1, isolated from the *Trypanosoma congolense* organism.

7. An isolated trans-sialidase obtainable from *Trypanosoma congolense*, characterized by one of the following amino acid part sequences:

```
TDTVKYSTDGGRTWKREVIIPNGR        (pos. 1 to 25 of
                                 SEQ ID NO: 2) or FRIPSLVEIDGVLIATFDTRYLRASDSSLI  (pos. 1 to 30 of
                                 SEQ ID NO: 4).
```

8. The isolated trans-sialidase of claim 7, wherein the isolated trans-sialidase consists of the amino acids of SEQ ID NO: 2 and is characterized by at least one of the following characteristics:

| | | |
|---|---|---|
|i)|Temperature optimum|30-40° C.|
|ii)|pH optimum|pH 6.5-8.5|
|iii)|Isoelectric point|pH 4-5|
|iv)|Molecular weight, native|400-600 kDa|
|v)|Molecular weight in the reducing SDS page|90 kDa.|

9. The isolated trans-sialidase of claim 7, wherein the isolated trans-sialidase consists of the amino acids of SEQ ID NO: 4 and is characterized by at least one of the following characteristics:

| | | |
|---|---|---|
|i)|Temperature optimum|30-40° C.|
|ii)|pH optimum|pH 6.5-8.5|

-continued

| | | |
|---|---|---|
| iii) | Isoelectric point | pH 5-6 |
| iv) | Molecular weight, native | 120-180 kDa |
| v) | Molecular weight in the reducing SDS page | 90 kDa. |

10. An isolated nucleotide sequence, encoding a trans-sialidase of claim 7.

11. An expression cassette, comprising, operatively linked to with at least one regulative nucleic acid sequence, a nucleic acid sequence of claim 10.

12. A recombinant vector, comprising at least one expression cassette of claim 11.

13. Procaryotic or eucaryotic host, transformed with at least one vector of claim 12.

14. A method for the enzymatic sialization of an acceptor molecule, characterized in that the acceptor molecule is incubated with a donor containing sialic acid residues in the presence of an enzyme of claim 7, and the sialylated acceptor is isolated.

15. The method of claim 14, characterized by at least one more of the following properties:
   a) the donor is selected from the group consisting of sialic acids bonded to oligosaccharides, polysaccharides, polysialic acids, glycoproteins and glycolipids.
   b) the acceptor is selected from the group consisting of polymers containing β-galactose, such as β-galactooligosaccharides, lactitol, lactobionic acid, methyl-β-lactoside, acetyllactosamines, galactopyranosides, trans-galactooligosaccharides, polygalactose and other glycoconjugates with terminally bonded β(1-3) or β(1-4) galactose or galactose.

16. A method for the isolation of an enzyme with trans-sialidase activity as defined in claim 7, comprising:
   cultivating *Trypanosoma congolense* in a medium so that said *Trypanosoma congolense* expresses the trans-sialidase,
   obtaining a culture supernatant containing said trans-sialidase, and isolating the trans-sialidase from the culture supernatant with exchange chromatography by applying a salt gradient.

17. The method of claim 16, additionally comprising isoelectric focussing, gel filtration, affinity chromatography and/or protein precipitation.

18. A foodstuff or food additive comprising the isolate of claim 7.

* * * * *

UNITED STATES PATENT AND TRADEMARK OFFICE
CERTIFICATE OF CORRECTION

PATENT NO. : 7,655,784 B2 Page 1 of 1
APPLICATION NO. : 10/538840
DATED : February 2, 2010
INVENTOR(S) : Schmitt et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 0 days.

Signed and Sealed this

Twenty-eighth Day of December, 2010

David J. Kappos
*Director of the United States Patent and Trademark Office*